(12) United States Patent
Zhu et al.

(10) Patent No.: US 12,390,153 B2
(45) Date of Patent: Aug. 19, 2025

(54) ULTRASOUND-TARGET-SHAPE-GUIDED SPARSE REGULARIZATION TO IMPROVE ACCURACY OF DIFFUSED OPTICAL TOMOGRAPHY

(71) Applicants: Quing Zhu, St. Louis, MO (US); Shiqi Xu, Durham, NC (US)

(72) Inventors: Quing Zhu, St. Louis, MO (US); Shiqi Xu, Durham, NC (US)

(73) Assignee: Washington University, St. Louis, MO (US)

( * ) Notice: Subject to any disclaimer, the term of this patent is extended or adjusted under 35 U.S.C. 154(b) by 779 days.

(21) Appl. No.: 16/850,763

(22) Filed: Apr. 16, 2020

(65) Prior Publication Data

US 2020/0330026 A1    Oct. 22, 2020

Related U.S. Application Data

(60) Provisional application No. 62/834,576, filed on Apr. 16, 2019.

(51) Int. Cl.
| | | |
|---|---|---|
| A61B 5/00 | (2006.01) | |
| A61B 8/00 | (2006.01) | |
| A61B 8/08 | (2006.01) | |

(52) U.S. Cl.
CPC .......... *A61B 5/4312* (2013.01); *A61B 5/0035* (2013.01); *A61B 5/0091* (2013.01); *A61B 8/0825* (2013.01); *A61B 8/4416* (2013.01)

(58) Field of Classification Search
None
See application file for complete search history.

(56) References Cited

U.S. PATENT DOCUMENTS

| | | |
|---|---|---|
| 6,956,650 B2 | 10/2005 | Boas et al. |
| 7,107,116 B2 | 9/2006 | Geng |
(Continued)

FOREIGN PATENT DOCUMENTS

| | | |
|---|---|---|
| WO | 201805444 A1 | 3/2018 |
| WO | 2019005722 A1 | 1/2019 |

OTHER PUBLICATIONS

L1-norm based nonlinear reconstruction improves quantitative accuracy of spectral diffuse optical tomography, vol. 9, No. 4, 2018, Biomedical optics express (Year: 2018).*
(Continued)

*Primary Examiner* — Shahdeep Mohammed
*Assistant Examiner* — Marjan Saboktakin
(74) *Attorney, Agent, or Firm* — Armstrong Teasdale LLP

(57) ABSTRACT

A diffuse optical tomography (DOT) system for generating a functional image of a lesion region of a subject includes a source subsystem configured to generate optical waves, a probe coupled to the source subsystem and configured to emit the optical waves generated by the source subsystem toward the lesion region and to detect optical waves reflected by the lesion region, a detection subsystem configured to convert the optical waves detected by the probe to digital signals, and a computing device including a processor and a memory. The memory includes instructions that program the processor to receive the digital signals sent from the detection subsystem, calculate an initial estimate of the functional image by solving an inverse optimization problem with a shape-regularized Fast Iterative Shrinkage-Thresholding algorithm (FISTA), reconstruct the functional image iteratively using a Finite Difference Method (FDM) or a Finite Element Method (FEM), and display the functional image.

17 Claims, 16 Drawing Sheets
(12 of 16 Drawing Sheet(s) Filed in Color)

(56) References Cited

U.S. PATENT DOCUMENTS

| | | |
|---|---|---|
| 7,729,750 B2 | 6/2010 | Tromberg et al. |
| 7,983,740 B2 | 7/2011 | Culver et al. |
| 9,134,229 B2 | 9/2015 | Lesage et al. |
| 9,867,542 B2 | 1/2018 | Wu et al. |
| 9,927,362 B2 | 3/2018 | Kumar et al. |
| 9,940,706 B2 | 4/2018 | Sekiguchi et al. |
| 9,964,747 B2 | 5/2018 | Ntziachristos et al. |
| 10,064,584 B2 * | 9/2018 | Yared .................... A61B 5/0059 |
| 2004/0215072 A1 * | 10/2004 | Zhu ........................ G01S 15/899 600/407 |
| 2010/0208965 A1 | 8/2010 | Jiang et al. |
| 2011/0137177 A1 | 6/2011 | Toma et al. |
| 2015/0066436 A1 | 3/2015 | Elliott et al. |
| 2015/0101411 A1 | 4/2015 | Zalev et al. |
| 2016/0278715 A1 | 9/2016 | Yu et al. |
| 2016/0282432 A1 | 9/2016 | Wang |
| 2018/0064347 A1 | 3/2018 | Adair et al. |
| 2020/0085382 A1 | 3/2020 | Taerum et al. |

OTHER PUBLICATIONS

Yao al. ("Simultaneous reconstruction of absorption and scattering distributions in turbid media using a born iterative method", SPIE vol. 2570, 1995) (Year: 1995).*

Yao al. ("Frequency-domain optical imaging of absorption and scattering distributions by a Born iterative method", Optical Society of America, 1997) (Year: 1997).*

* cited by examiner

ULTRASOUND-TARGET-SHAPE-GUIDED SPARSE REGULARIZATION TO IMPROVE ACCURACY OF DIFFUSED OPTICAL TOMOGRAPHY

CROSS REFERENCE TO RELATED APPLICATION

This application claims the benefit of U.S. Provisional Application No. 62/834,576, filed Apr. 16, 2019, entitled "ULTRASOUND-TARGET-SHAPE-GUIDED SPARSE REGULARIZATION TO IMPROVE ACCURACY OF DIFFUSED OPTICAL TOMOGRAPHY FOR BREAST CANCER DIAGNOSIS" which is hereby incorporated by reference in its entirety herein.

GOVERNMENTAL SUPPORT

This invention was made with government support under EB002136 awarded by the National Institutes of Health. The government has certain rights in the invention.

BACKGROUND

The present disclosure generally relates to imaging systems. Among the various aspects of the present disclosure is the provision of an imaging system. Other objects and features will be in part apparent and in part pointed out hereinafter.

Diffuse optical tomography (DOT) is a non-invasive functional imaging modality that utilizes near-infrared (NIR) light to image biological tissue. In DOT imaging, tissue is illuminated with diffused light, and the reflected or transmitted light is measured at the tissue surface. The tissue's optical properties are then estimated with image reconstruction algorithms. In the past decades, DOT has been actively studied for diagnosis of breast cancer and assessment of treatment response. Clinical studies have demonstrated that the hemoglobin (Hb) concentration (oxy-Hb, deoxy-Hb, and total Hb) calculated from DOT reconstructed absorption images is directly related to breast tumor angiogenesis, and is used to differentiate cancers from benign lesions as well as to assess breast cancer treatment response.

However, due to the intense light scattering in breast tissue, lesion localization is quite challenging and multimodality imaging systems have been developed to assist in reconstructing more informative DOT images. Recently, ultrasound-guided DOT has emerged as a promising low-cost adjunct technique to ultrasound (US) for the diagnosis of breast cancers and assessment of breast cancer neoadjuvant chemotherapy response, where a priori lesion location information provided by coregistered US images is used to assist DOT reconstruction. US-guided DOT is best implemented in reflection geometry, which is compatible with conventional US pulse-echo imaging. Additionally, the light propagation depth is reduced to several centimeters when the patient is in a supine position, favoring reflection mode imaging.

In breast DOT reconstruction, linear Born approximation is widely used in the art to compute the weight matrix for modeling the forward problem. With background optical properties estimated from the contralateral breast or a homogeneous medium, the weight matrix can be computed analytically and optimization methods can be used to search for the lesion absorption distribution iteratively. A problem with linear Born approximation is the tendency to underestimate the absorption coefficients when the lesion is large and highly absorbing.

Sparse regularization is a newer approach for improving DOT reconstruction accuracy and robustness. Because of the intense light scattering, the DOT image reconstruction problem is usually ill-posed. Examples of known developed DOT algorithms include being based on edge-preserving total variation (TV) regularization or forming the imaging problem as a joint sparsity recovery problem.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF DESCRIPTION

A diffuse optical tomography (DOT) system for generating a functional image of a lesion region of a subject is described. The DOT system includes a source subsystem configured to generate optical waves, a probe coupled to the source subsystem and configured to emit the optical waves generated by the source subsystem toward the lesion region and to detect optical waves reflected by the lesion region, a detection subsystem configured to convert the optical waves detected by the probe to digital signals, and a computing device including a processor and a memory. The memory including instructions that program the processor to receive the digital signals sent from the detection subsystem, calculate an initial estimate of the functional image by solving an inverse optimization problem with a target shape (depth, width)-regularized Fast Iterative Shrinkage-Thresholding algorithm (FISTA), reconstruct the functional image iteratively using a Finite Difference Method (FDM) or Finite Element Method (FEM), and display the functional image.

Further, a method for generating a functional image of a lesion region of a subject using diffuse optical tomography (DOT) is described. The method includes emitting optical waves toward the lesion region, detecting optical waves reflected by the lesion region and converting the optical waves to digital signals, calculating an initial estimate of the functional image by solving an inverse optimization problem with a target-shape regularized Fast Iterative Shrinkage-Thresholding algorithm (FISTA), reconstructing the functional image iteratively using a Finite Difference Method (FDM) or Finite Element Method (FEM), and displaying the functional image.

Further, at least one non-transitory computer-readable storage media having computer-executable instructions embodied thereon for generating a functional image of a lesion region of a subject using diffuse optical tomography (DOT) is described. When executed by at least one processor, the computer-executable instructions cause the processor to emit optical waves toward a lesion region of the subject, detect optical waves reflected by the lesion region and converting the optical waves to digital signals, calculate an initial estimate of the functional image by solving an inverse optimization problem with a target shape-regularized Fast Iterative Shrinkage-Thresholding algorithm (FISTA), reconstruct the functional image iteratively using a Finite Difference Method (FDM) or Finite Element Method (FEM); and display the functional image.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination

DESCRIPTION OF THE DRAWINGS

The patent or application file contains at least one drawing executed in color. Copies of this patent or patent application publication with color drawing(s) will be provided by the Office upon request and payment of the necessary fee.

The following drawings illustrate various aspects of the disclosure.

Those of skill in the art will understand that the drawings, described below, are for illustrative purposes only. The drawings are not intended to limit the scope of the present teachings in any way. Like reference symbols in the various drawings indicate like elements.

DETAILED DESCRIPTION

A novel depth-dependent $\ell_1$ regularized non-linear Born iterative reconstruction method for US-guided DOT is introduced. This approach iteratively updates the photon-density wave using a finite difference method and computes the weight matrix based on Born approximation. Phantom and patient data are used to compare the results with those obtained using the first order linear Born method and experiments demonstrate that the proposed method reconstructs the absorption distribution more accurately than linear Born.

Methods and systems are disclosed for an Ultrasound (US)-guided diffuse optical tomography (DOT) based imaging technique. The methods use US-guided depth and width dependent $\ell 1$ sparse regularization for improving DOT reconstruction by incorporating a priori lesion depth and shape information from a co-registered US image. The methods and systems as disclosed herein allow for reconstruction of an absorption map using the target shape-regularized fast iterative shrinkage-thresholding optimization algorithm (FISTA) and are validated using both phantom and patient data. Further, the methods provide more accurate target absorption reconstruction and better resolution than current methods, which allow for a generalized method for breast cancer diagnosis.

Figure 1:
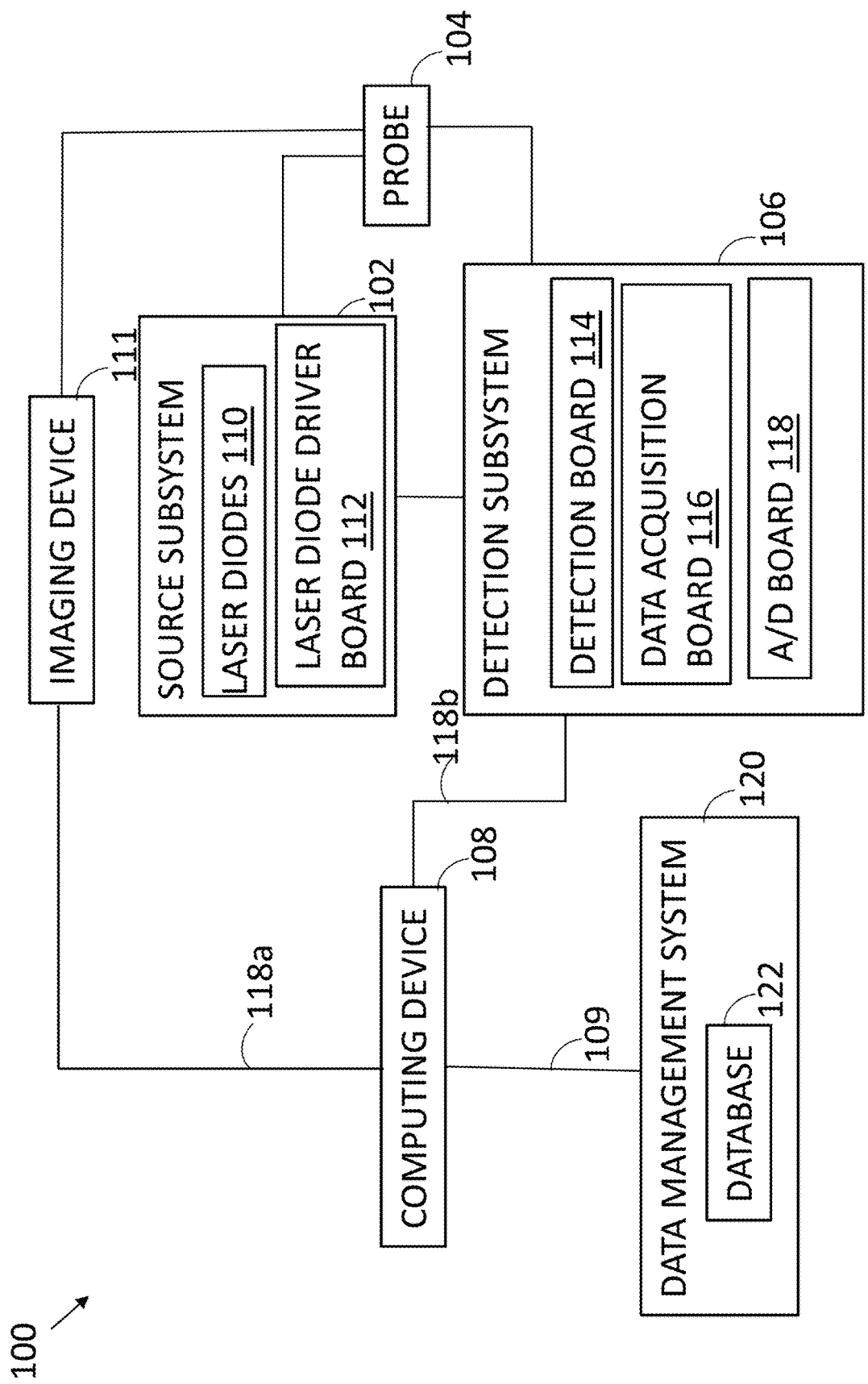
FIG. 1 is a block diagram showing an imaging system in accordance with an aspect of the disclosure.

In various aspects, the disclosed methods may be implemented using a computing device as part of an imaging system. As seen in FIG. 1, DOT system 100 includes an imaging device 111 that is configured to acquire imaging data of target region positioned within a body region of a subject (not shown). A subject as used herein is a human (live or deceased), an animal (live or deceased), an organ or part of an organ of a human or an animal, or part of a human or an animal. For example, a body region may be a breast, a part of a human that includes an ovary or a cervix, or part of a human that includes a lesion or part of a lesion. The imaging device may be an ultrasound (US)-guided diffuse optical tomography (DOT) device.

Although, in some of the examples provided below, the systems and methods disclosed herein are used on certain part of the body or certain types of lesions, the systems and methods are not limited to that part of human or animal body or that type of lesions.

FIG. 1 is a block diagram of an example compact DOT system 100. System 100 includes a source subsystem 102, a probe 104, a detection subsystem 106, and a computing device 108. DOT system 100 includes, but is not limited to, a near-infrared (NIR) diffuse optical tomography device or an NIR imager. Source subsystem 102 includes a plurality of laser diodes 110 and a laser diode driver board 112. Laser diodes 110 are configured to generate NIR optical waves. Laser diode driver board 112 is configured to drive diodes 110. Probe 104 is configured to emit the optical waves generated by source subsystem 102 toward a lesion region of the subject. Probe 104 is also configured to detect optical waves reflected by the lesion region. In various embodiments, the light spectrum used in system 100 is at the near-infrared spectrum (wavelength from approximately 700 to approximately 900 nm). NIR DOT imaging is a noninvasive imaging technique that uses NIR light to estimate optical properties of tissue. Within the NIR spectrum, oxygenated and deoxygenated hemoglobin are major chromophores absorbing light and can be used to characterize tumor vasculature, which is directly related to tumor angiogenesis.

In the exemplary embodiment, laser diodes 110 are configured to emit optical waves of a plurality of wavelengths toward an imaging volume of the subject. In various embodiments, laser diodes 110 are configured to emit optical waves at wavelengths 740, 780, 808 and 830 nm. The imaging volume includes a lesion region.

In the exemplary embodiment, detection subsystem 106 includes a detection board 114 and an analog-to-digital (A/D) board 116. Detection board 114 includes one or more photomultiplier tubes (PMT) configured to convert optical waves detected by probe 104 to electrical signals. A/D board 116 is configured to convert electrical signals outputted from detection board 114 to digital signals. Computing device 108 is configured to receive the digital signals from detection subsystem 106 and reconstruct them into functional image of the lesion region. Computing device 108 is also configured to display the reconstructed functional image.

In operation, optical waves generated by source subsystem 102 are sent to probe 104 and emitted toward a lesion region of the subject via probe 104. Probe 104 detects optical waves reflected by the lesion region. The detected signals are sent to detection subsystem 106 and converted to electrical signals. The electrical signals are then converted to digital signals by AD board 116. The digital signals are received in computing device 108 and reconstructed into a functional image of the lesion region. The reconstructed image is also displayed by computing device 108.

In the example embodiment, system 100 is a guided DOT system. That is, system 100 further includes an imaging device 111 that is configured to acquire guiding data of a subject including the lesion region of the subject. Imaging device 111 may be any suitable imaging device that makes use of an imaging modality different from DOT, including, but not limited to, an ultrasound device, a magnetic resonance imaging system, an x-ray device, or a computed tomography device. In various embodiments, imaging device 111 acquires data also through probe 104 when the imaging modality of imaging device 111 is US.

In the example embodiment, computing device 108 is coupled to imaging device 111 via a data conduit 118a and operatively coupled to detection subsystem 106 via a data conduit 118b. It should be noted that, as used herein, the term "couple" is not limited to a direct mechanical, electrical, and/or communication connection between components, but may also include an indirect mechanical, electrical, and/or communication connection between multiple components. Although one computing device 108 is depicted in FIG. 1, two or more computing devices may be used in the system. Imaging device 111 and detection subsystem 106 may be in communication with different computing devices (not shown) and the computing devices are in communication with each other.

Imaging device 111 and detection subsystem 106 may communicate with computing device 108 using a wired network connection (e.g., Ethernet or an optical fiber via a universal serial bus port on computing device 108), a wireless communication means, such as radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a short-range wireless communication channel such as BLUETOOTH®, a cellular phone technology (e.g., the Global Standard for Mobile communication (GSM)), a satellite communication link, and/or any other suitable communication means. IEEE is a registered trademark of the Institute of Electrical and Electronics Engineers, Inc., of New York, New York WIMAX is a registered trademark of WiMax Forum, of Beaverton, Oregon BLUETOOTH is a registered trademark of Bluetooth SIG, Inc. of Kirkland, Washington System 100 may further include a data management system 120 that is coupled to computing device 108 via a network 109. In some embodiments, computing device 108 includes a data management system 120. Data management system 120 may be any device capable of accessing network 109 including, without limitation, a desktop computer, a laptop computer, or other web-based connectable equipment. More specifically, in the exemplary embodiment, data management system 120 includes a database 122 that includes previously acquired data of other subjects. In the exemplary embodiment, database 122 can be fully or partially implemented in a cloud computing environment such that data from the database is received from one or more computers (not shown) within system 100 or remote from system 100. In the exemplary embodiment, the previously acquired data of the other subjects may include, for example, a plurality of measurements of lesion region of other subjects. Database 122 can also include any additional information of each of the subjects that enables system 100 to function as described herein Referring again to FIG. 1, computing device 108 is configured to receive imaging data from the imaging device 111. The computing device 108 may be configured to control the imaging device 111. The computing device may include a number of components which perform specific tasks including, but not limited to, a processor, a data storage device and/or a communication component. In one aspect, the data storage device is configured to store data received or generated by computing device, such as any of the data stored in a database or any outputs of processes implemented by any component of the computing device. In another aspect, the communication component is configured to enable communications between the computing device and other devices over a network or a plurality of network connections using predefined network protocols such as TCP/IP (Transmission Control Protocol/Internet Protocol).

Figure 2:
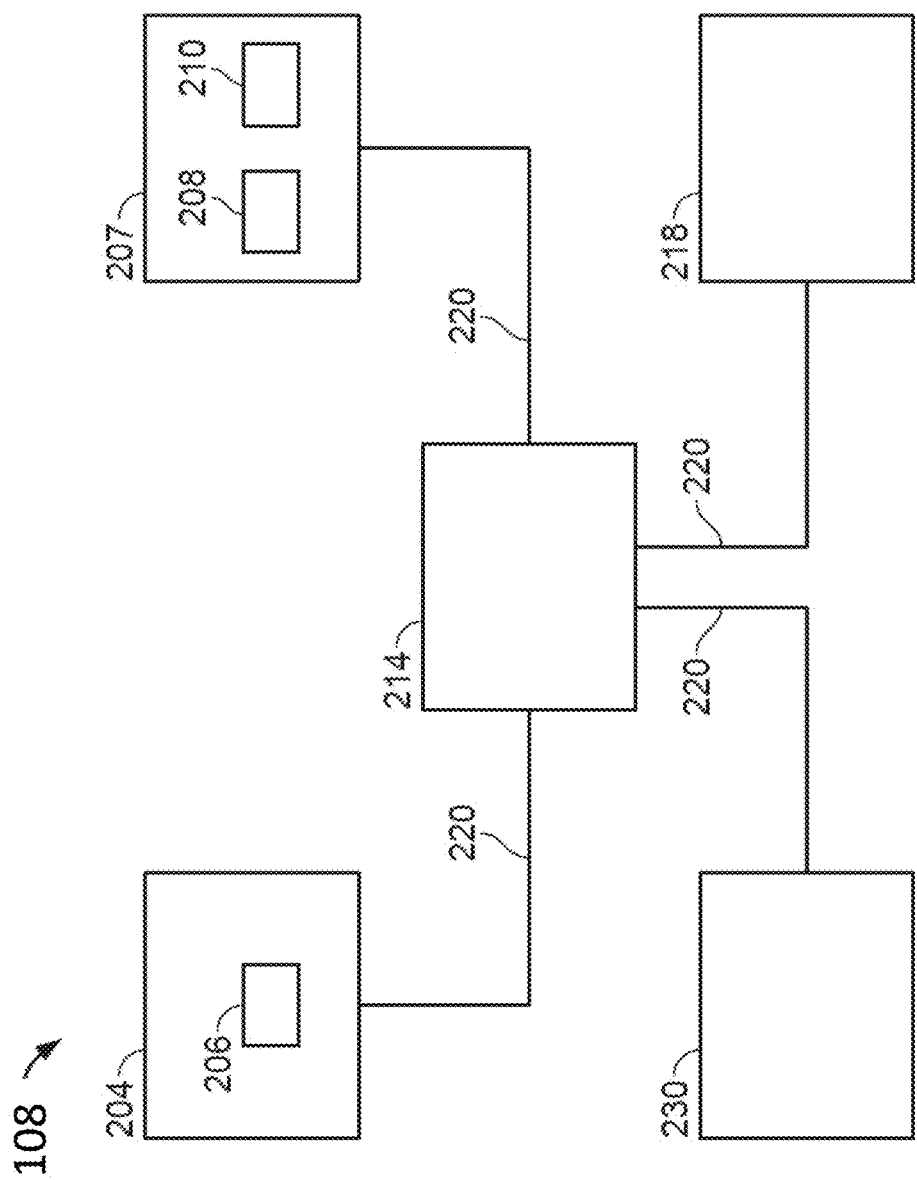
FIG. 2 is a block diagram illustrating a computing device in accordance with an aspect of the disclosure.

FIG. 2 is a block diagram of computing device 108. In the exemplary embodiment, computing device 108 includes a user interface 204 that receives at least one input from a user, such as an operator of imaging device 111 or system 100. User interface 204 may include a keyboard 206 that enables the user to input pertinent information. User interface 204 may also include, for example, a pointing device, a mouse, a stylus, a touch sensitive panel (e.g., a touch pad or a touch screen), a gyroscope, an accelerometer, a position detector, and/or an audio input interface (e.g., including a microphone).

Moreover, in the exemplary embodiment, computing device 108 includes a presentation interface 207 that presents information, such as input events and/or validation results, to the user. Presentation interface 207 may also include a display adapter 208 that is coupled to at least one display device 210. More specifically, in the exemplary embodiment, display device 210 may be a visual display device, such as a cathode ray tube (CRT), a liquid crystal display (LCD), an organic LED (OLED) display, and/or an "electronic ink" display. Alternatively, presentation interface 207 may include an audio output device (e.g., an audio adapter and/or a speaker) and/or a printer.

Computing device 108 also includes a processor 214 and a memory device 218. Processor 214 is coupled to user interface 204, presentation interface 207, and to memory device 218 via a system bus 220. In the exemplary embodiment, processor 214 communicates with the user, such as by prompting the user via presentation interface 207 and/or by receiving user inputs via user interface 204. The term "processor" refers generally to any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 218 includes one or more devices that enable information, such as executable instructions and/or other data, to be stored and retrieved. Moreover, memory device 218 includes one or more computer readable media, such as, without limitation, dynamic random access memory (DRAM), static random access memory (SRAM), a solid state disk, and/or a hard disk. In the exemplary embodiment, memory device 218 stores, without limitation, application source code, application object code, configuration data, additional input events, application states, assertion statements, validation results, and/or any other type of data. Computing device 108, in the exemplary embodiment, may also include a communication interface 230 that is coupled to processor 214 via system bus 220. Moreover, communication interface 230 is communicatively coupled to imaging device 111, detection subsystem 106, and data management system 120.

In the exemplary embodiment, processor 214 may be programmed by encoding an operation using one or more executable instructions and providing the executable instructions in memory device 218. In the exemplary embodiment, processor 214 is programmed to select a plurality of measurements that are received from imaging device 111 or detection subsystem 106. The plurality of measurements may include, for example, a plurality of voxels of at least one image of the subject, wherein the image may be generated by processor 214 within computing device 108. The image may also be generated by an imaging device (not shown) that may be coupled to computing device 108 and imaging device 111, wherein the imaging device may generate the image based on the data received from imaging device 111 or detection subsystem 106 and then the imaging device may transmit the image to computing device 108 for storage within memory device 218. Alternatively, the plurality of measurements may include any other type measurement of the lesion region that enables system 100 to function as described herein.

In other aspects, the processor is configured to execute instructions received from a storage device. In some aspects, executable instructions may be stored in the storage device. The processor may include one or more processing units (e.g., in a multi-core configuration). The storage device may be any device allowing information such as executable instructions and/or other data to be stored and retrieved. In one aspect, the computer-readable instructions, when executed on a processor, may provide a user interface to the user via the media output component. The user interface may further receive and process input from the input device. The user interface may include, but is not limited to, a web browser and an application. The storage device may include one or more computer-readable media.

In some aspects, the processor may be operatively coupled to a storage device via a storage interface. The storage interface may be any component capable of providing the processor with access to storage device. Non-limiting examples of suitable storage interfaces include an Advanced Technology Attachment (ATA) adapter, a Serial ATA (SATA) adapter, a Small Computer System Interface (SCSI) adapter, a RAID controller, a SAN adapter, a network adapter, and/or any component providing the processor with access to the storage device.

Non-limiting examples of storage devices include random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM).

In some aspects, the computing device may include an input device for receiving input from the user. The input device may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen may function as both an output device of the media output component and the input device.

System 100 further includes a data management system 108 that is coupled to computing device 104 via a network 109. In some embodiment, the computing device 104 includes a data management system 108. Data management system 108 may be any device capable of accessing network 109 including, without limitation, a desktop computer, a laptop computer, or other web-based connectable equipment. More specifically, in the exemplary embodiment, data management system 108 includes a database 110 that includes previously acquired data of other subjects. In the exemplary embodiment, database 110 can be fully or partially implemented in a cloud computing environment such that data from the database is received from one or more computers (not shown) within system 100 or remote from system 100. In the exemplary embodiment, the previously acquired data of the other subjects may include, for example, a plurality of measurements of lesion region of other subjects. Database 110 can also include any additional information of each of the subjects that enables system 100 to function as described herein.

System 100 is an exemplary embodiment for implementing the novel method of depth-dependent $\ell_1$ regularized non-linear Born iterative reconstruction method for US-guided DOT. The following is a discussion of how to solve the individual sub-problems of the method and combine them together including formulating and solving the inverse problem, using the estimated optical properties to correct the photon-density wave estimation, and establishing the proposed algorithm and method implementing the algorithm for DOT reconstruction.

Dual-Grid Born Approximation

NIR photon migration in breast tissue can be modeled by the frequency-domain diffusion equation of the photon-density wave. Assuming optical properties change smoothly inside the breast tissue, the frequency-domain diffusion equation may be approximated as a Holmholtz equation, $$\nabla^2 U(r) + k^2(r)U(r) = -S(r), \quad \text{(Eq. 1)}$$

where $U(r)$ is the photon-density wave and $S(r)$ is the source distribution normalized by the diffusion coefficient. The wavenumber is given as $$k(r) = \sqrt{\left(\frac{i\omega}{v} - \mu_a(r)\right)\Big/ D(r)}, \quad \text{(Eq. 2)}$$

where $\mu_a(r)$ and $D(r) = 1/[3(\mu_a(r)+\mu'_s(r))]$ are the absorption and diffusion coefficient distributions, respectively. Further, $\mu'_s(r)$ is the reduced scattering coefficient distribution, $v$ is the speed of light in tissue, and $w$ is the modulation frequency of the photon-density wave. $U(r, r_s) = U_0(r, r_s) + U_{sc}(r, r_s)$, where $U_0(r, r_s)$ represents the photon-density wave in a homogeneous medium with constant background optical properties $\mu_{a0}$ and $\mu'_{s0}$, and $U_{sc}(r, r_s)$ represents the perturbed photon-density wave due to heterogeneities. $U_{sc}(r, r_s)$ can be written in an integral form as $$U_{SC}(r, r_s) = \int U(r', r_s) O(r') G(r - r') dr', \quad \text{(Eq. 3)}$$

in which $G(\cdot)$ is the Green's function satisfying the extrapolated boundary condition. Since there are no analytical solutions for the photon-density wave distribution $U(r, r_s)$ in an inhomogeneous medium, it is approximated with a numerical method. It is further assumed the reduced scattering coefficient varies slowly inside the human breast, and is significantly higher than the absorption coefficient; hence the diffusion coefficient distribution is approximated with the diffusion constant $D(r) = 1/(3(\mu_{a0}(r)+\mu'_{s0}(r)))$. Moreover, $k_0$ and $O(r)$ can be written as $$k_0 = \sqrt{\left(\frac{i\omega}{v} - \mu_{a0}\right)\Big/ D_0}, \quad O(r) = -\frac{\delta\mu_a(r)}{D_0}. \quad \text{(Eq. 4)}$$

In US-guided DOT reconstruction, to improving the ill-posed inverse problem, a dual grid schedule is used for discretizing the lesion volume with a fine grid and the background volume with a coarse grid. Thus, the integration in eq. (3) can be formulated in matrix form as $$y = Wx + \epsilon, \quad \text{(Eq. 5)}$$

where $W \in C^{M \times N} = [W_L, W_B]$, $x \mathbb{R}^N = [X_L; X_B]$, $y \in C^{M \times N}$ is the measurement, and $\epsilon$ the measurement noise. $[\bullet, \bullet]$ and $[\bullet; \bullet]$ are the horizontal and vertical matrix concatenations, respectively. Also, and $X_L \in \mathbb{R}^{N_L}$ and $X_B \in \mathbb{R}^{N_B}$ are vectors representing the absorption coefficient distributions of the lesion and the background volume, respectively. Further $$W_L = \left[-\frac{1}{D_0} G(r_{vj}, r_{di}) U(r_{vj}, r_{si})\right]_{M \times N_L} \quad \text{(Eq. 6)}$$

and $$W_B = \left[-\frac{1}{D_0} G(r_{vj}, r_{di}) U(r_{vj}, r_{si})\right]_{M \times N_B} \quad \text{(Eq. 7)}$$

are weight matrices for the lesion and the background volume, respectively.

Gradient-Based Reconstruction

With the definition of W, x, and y above, the inverse problem is formulated as $$\hat{x} = \underset{x \in \mathbb{R}^N}{\operatorname{argmin}} \left\{ \frac{1}{2} \|y - Wx\|_2^2 + \|\operatorname{diag}(\lambda)x\|_1 \right\}, \quad \text{Eq. (8)}$$

where $y \in C^M$ is the measurement, $x \in \mathbb{R}^N$ is the absorption distribution, and $\lambda \in \mathbb{R}^N$ is a vector of depth-dependent non-negative regularization parameters determined from the lesion height information given by the co-registered ultrasound image. The first term, $D(x) = \frac{1}{2}\|y - Wx\|_2^2$, measures the data fidelity of the forward model, while the $\ell_1$-term, $R(x) = \|\operatorname{diag}(\lambda)x\|_1$, promotes the sparsity level of the reconstructed images. Each element of the vector $\lambda$ is empirically chosen as $$\frac{0.01}{d_i^2},$$

where $d_i$ is the width of the tumor at the depth of the $i^{th}$ reconstruction slice, measured in centimeters from the co-registered US image. In another approach. $\lambda i = c/(d_i^2 \times \text{depth}^i)$, where c is the radius of the DOT imaging probe size. The optimization problem described in Eq. (8) is solved with the fast iterative shrinkage-thresholding algorithm (FISTA). FISTA is a widely used proximal gradient method with Nesterov's acceleration. The proximal gradient method solves the optimization problem with a gradient step followed by a proximal step. Using FISTA has the advantages of being relatively economical to compute and having a faster convergence rate than at least some other first order optimization methods. The reconstruction method of the inverse problem is encapsulated in Algorithm 1, below.

| Algorithm 1 Sparsely regularized DOT reconstruction |
|---|
| 1: input: initial guess $\hat{x}^0 = 0$, weight matrix W, step size $\tau$, regularization parameters $\lambda$ |
| 2: set: $s_0 \leftarrow \hat{x}^0$, $q_0 \leftarrow 1$ |
| 3: for $t = 1, 2, \ldots$ do |
| 4: $\quad z^t \leftarrow s^{t-1} - \tau \nabla \mathcal{D}(s^{t-1})$ ▷ (9) |
| 5: $\quad \hat{x}^t \leftarrow \operatorname{prox}_R(z^t, \tau\lambda)$ ▷ (11) |
| 6: $\quad q_t \leftarrow \frac{1}{2}(1 + \sqrt{1 + 4q_{t-1}^2})$ |
| 7: $\quad s^t \leftarrow \hat{x}^t + ((q_{t-1} - 1)/q_t)(\hat{x}^t - \hat{x}^{t-1})$ |
| 8: $\quad t \leftarrow t + 1$ |
| 9: end for |
| 10: return: $\hat{x}^t$ |

A zero initialization is used for the absorption coefficient distribution x. The intermediate variables s and q are also initialized accordingly, as described in step 2. The iteration is then started. The gradient of D(x) in step 4 can be calculated as $$\frac{\partial}{\partial x}\mathcal{D}(x) = W^H(Wx - y),\quad \text{(eq. 9)}$$

and $\tau$ is the step size for the proximal gradient method, where $W^H$ is the Hermitian adjoint of W. For the experiments reported in this article, $\tau=1/\text{norm}(W^H W)$ is used. In step 5, after updating the intermediate variable z', c $\hat{x}^t$ is constrained using the proximal operator associated with the convex regularization term R(x), defined as $$prox_{\mathcal{R}}(x) = \underset{z \in \mathbb{R}^N}{\arg\min}\left\{\mathcal{R}(x) + \frac{1}{2}\|x - z\|_2^2\right\},\quad \text{(Eq. 10)}$$

This proximal operator can be efficiently calculated with the soft threshold function $S\gamma(z)$, defined as $$S_\gamma(z) = \text{sgn}(z) \odot \max(0, |z|-\gamma).\quad \text{(Eq. 11)}$$

where $\odot$ is the element-wise multiplication operator and $\gamma=\tau\lambda$. Here, sgn(·) is the sign function that extracts the sign of a real number, and |·| calculates the absolute value of each element in z. The intermediate variables s' and $q_r$ are then updated following the procedures listed as step 6 and step 7, which help accelerate the convergence rate.

Finite Difference Photo-Density Wave Estimation

The photon-density wave required for formulating the Born weighting matrices in Eq. (3) can be estimated with the finite difference method. Cartesian coordinates are used to discretize the volume and approximate the differential operations with Frechet derivatives so Eq. (1) can be numerically written as $$\frac{U_{i+1,j,k} + U_{i-1,j,k}}{\Delta x^2} + \frac{U_{i,j+1,k} + U_{i,j-1,k}}{\Delta y^2} + \frac{U_{i,j,k+1} + U_{i,j,k-1}}{\Delta z^2} - \left(\frac{2}{\Delta x^2} + \frac{2}{\Delta y^2} + \frac{2}{\Delta z^2} - k_{i,j,k}^2\right)U_{i,j,k} = -S_{i,j,k},\quad \text{(Eq. 12)}$$

where i, j, and k are indices along the x, y, and z directions; $U_{i,j,k}$ is the discrete sample of the photon-density wave U(r) at the <i, j, k> position; and $S_{i,j,k}$ is the source distribution. By defining u and s as vector representations of the distributions of photon-density wave U and the sources, respectively, Eq. (12) can be implemented as a linear operation on the photon-density wave u, $$Lu = s,\quad \text{(Eq. 13)}$$

where L is the system matrix, which depends on the optical property distribution of the medium. The above calculation can also be implemented using Finite Element Method (FEM). The initial photon-density wave distribution is calculated with estimated background optical properties from the contralateral breast, using a known fitting method. After constructing the matrix L based on the estimated absorption distribution, the photon-density wave distribution is updated using the conjugate gradient method. Because the absorption coefficients in the coarse-grid region are very close to the background, the photon-density wave is updated only inside the fine-grid area.

Figure 3A:
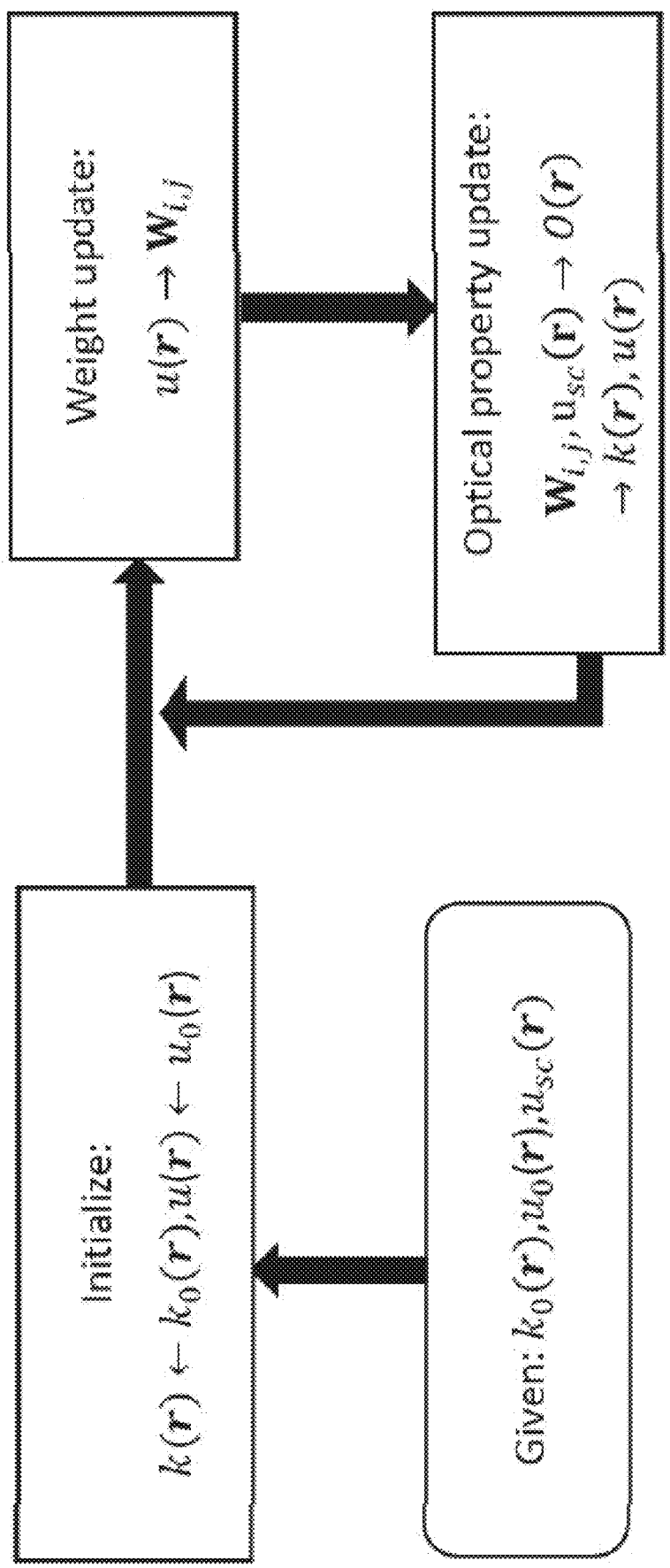
FIG. 3A is a flowchart of a proposed algorithm that combines depth-dependent, target-width-dependent sparse regularization with a non-linear Born iterative method.

FIG. 3A is a flowchart of the proposed algorithm that combines depth-dependent sparse regularization with a non-linear Born iterative method. First, the lesion absorption is reconstructed by solving the inverse problem using the shape-regularized FISTA. The strength of $\ell 1$ regularization for each depth is determined by the depth and the width of the lesion, measured from the co-registered US images. Then the photon-density wave is re-calculated using the finite-difference method to obtain updated estimations of the weight matrix and the target absorption distribution. Given the perturbed photon-density wave measurement $u_{sc}(r)$, the wavenumber distribution k(r) and the photon-density wave distribution u(r) are initialized with those of the homogeneous background media. The photon-density wave distribution is used to form the weight matrix W. The absorption coefficient distribution O(r) is reconstructed and the photon-density wave u(r) and wave number k(r) distributions are recalculated. The second and third steps are repeated until adequate iterations are reached. In the example embodiment, the iteration stops after 10 iterations. In other embodiments the iteration may stop after any suitable number of iterations greater or less than 10 iterations.

Figure 3B:
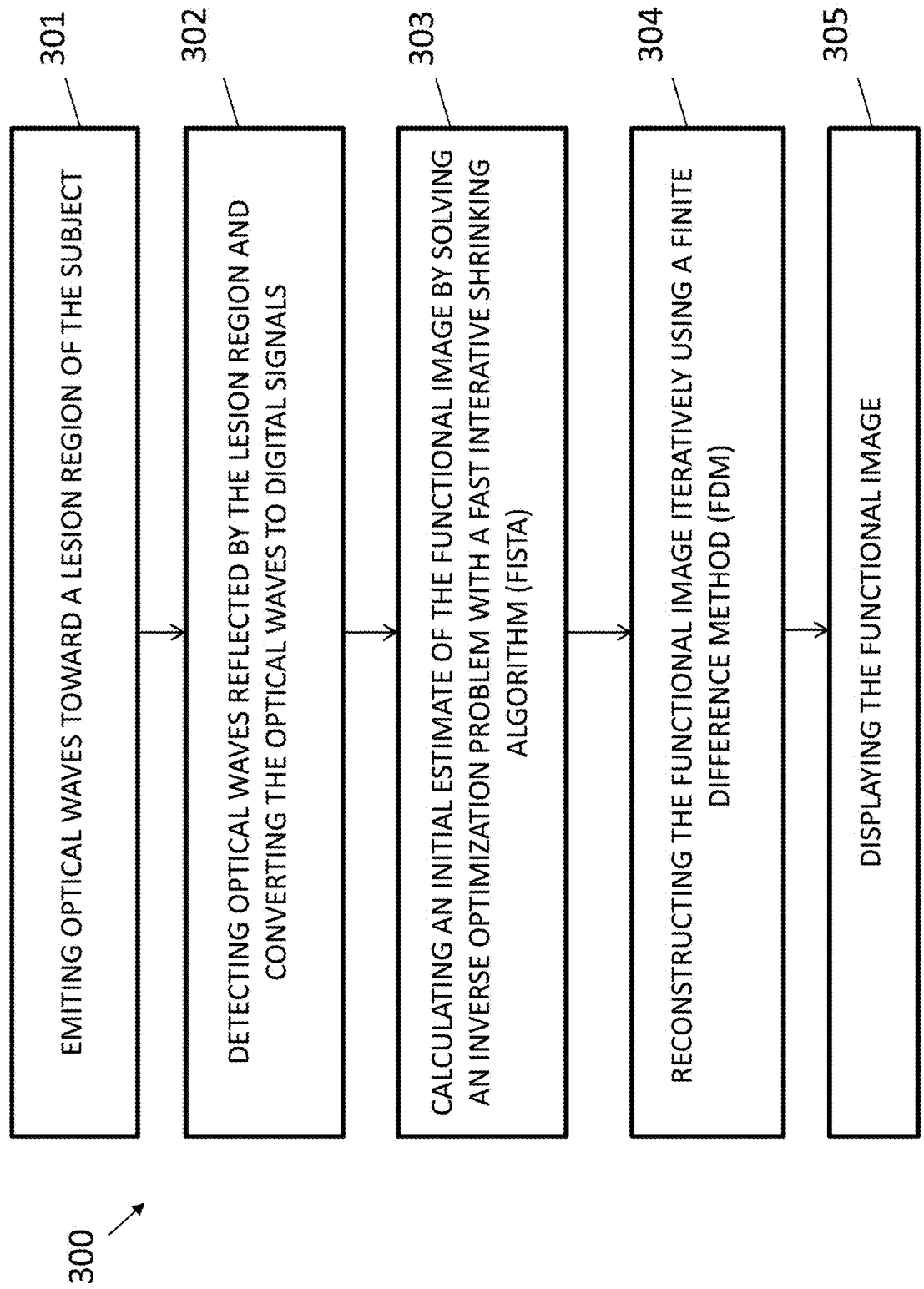
FIG. 3B is a flowchart of a proposed method implementing the algorithm shown in FIG. 3A.

FIG. 3B is a flowchart of the proposed method 300 implementing the algorithm shown in FIG. 3A. the method 300 includes 301 emitting optical waves toward the lesion region, 302 detecting optical waves reflected by the lesion region and converting the optical waves to digital signals 303 calculating an initial estimate of the functional image by solving an inverse optimization problem with a shape-regularized Fast Iterative Shrinkage-Thresholding algorithm (FISTA), 304 reconstructing the functional image iteratively using a Finite Difference Method (FDM), and 305 displaying the functional image.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

To perform imaging experiments, a US-guided DOT system which consists of a NIR imaging system and an US system. Four laser diodes at wavelengths of 740, 780, 808, and 830 nm are used to generate NIR light modulated at a 140 MHz carrier frequency. The light is then multiplexed to nine positions and delivered to the medium sequentially. Fourteen parallel photo-multiplier detector (PMT) tubes detect the reflected light from the medium. A custom-made A/D board digitizes the fourteen-channel data Phantom experiments and patient studies were conducted to evaluate the performance of the proposed algorithm. Phantom experiments were used to validate both the accuracy and resolution of the proposed method. Phantom targets having different optical contrasts were first submerged in an intralipid solution. The high contrast target was made of material with $\mu_a=0.23$ cm$^{-1}$ and $\mu'_s=7$ cm$^{-1}$, while for the low contrast target material, $\mu_a=0.11$ cm$^{-1}$ and $\mu'_s=7.5$ cm$^{-1}$. Three spherical targets with diameters of 1, 2, and 3 cm at depths of 0.5, 1.0, 1.5, and 2.0 cm were submerged. These depths were measured at the surface of the target using co-registered US images. The intralipid solution had an absorption coefficient $\mu_{a0}$=0.02-0.03 cm$^{-1}$ and a reduced scattering coefficient $\mu_s'$=7-8 cm$^{-1}$, which were acquired by fitting.

The resolution of the proposed algorithm was explored by submerging two 1.0 cm diameter high contrast ($\mu_a$=0.23 cm$^{-1}$) spherical targets inside the intralipid solution at 1.5 cm depth. The two balls were both placed in the center region along the US B-scan direction. Finally, the performance of the proposed algorithm was tested using data from 20 patients, of which 10 patients had malignant lesions, and 10 patients had benign lesions, based on biopsy results. Both the lesion and the normal contralateral breast were imaged with the US-guided DOT system. Measurements from the contralateral normal breast were used to estimate the average background optical properties of the breast.

Figure 4A:
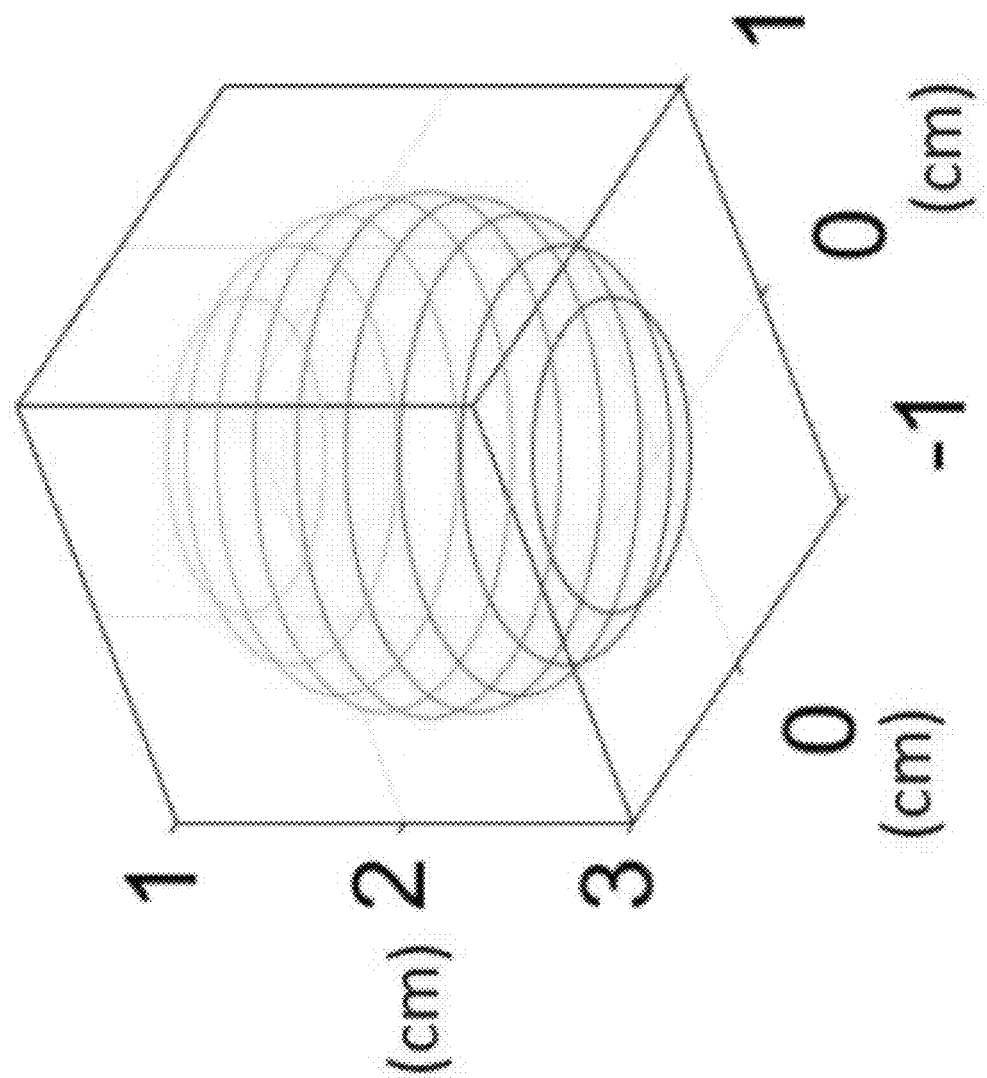
FIG. 4A is a 3D contour plot of a phantom target.
Figure 4B:
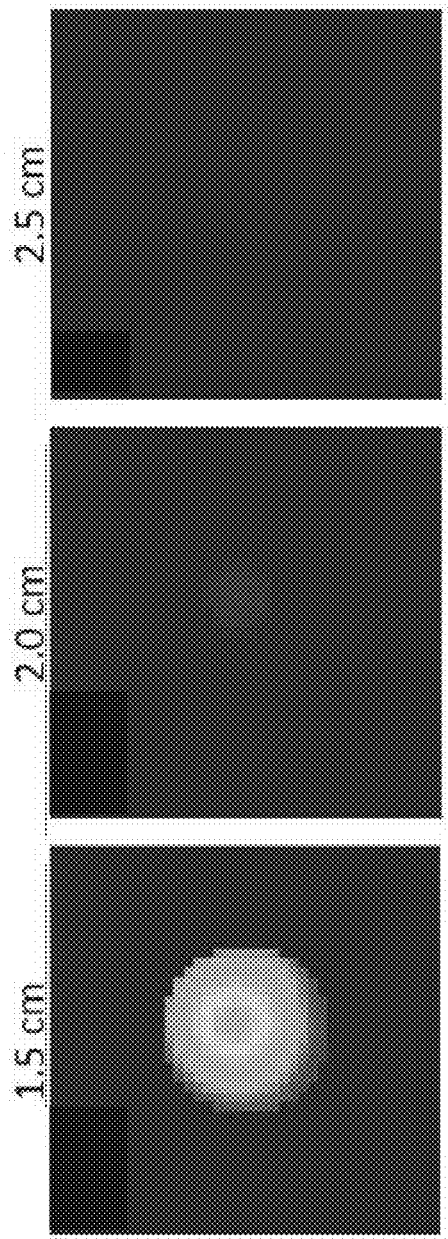
FIG. 4B is a reconstruction of one 2 cm diameter ball using linear Born method
Figure 4C:
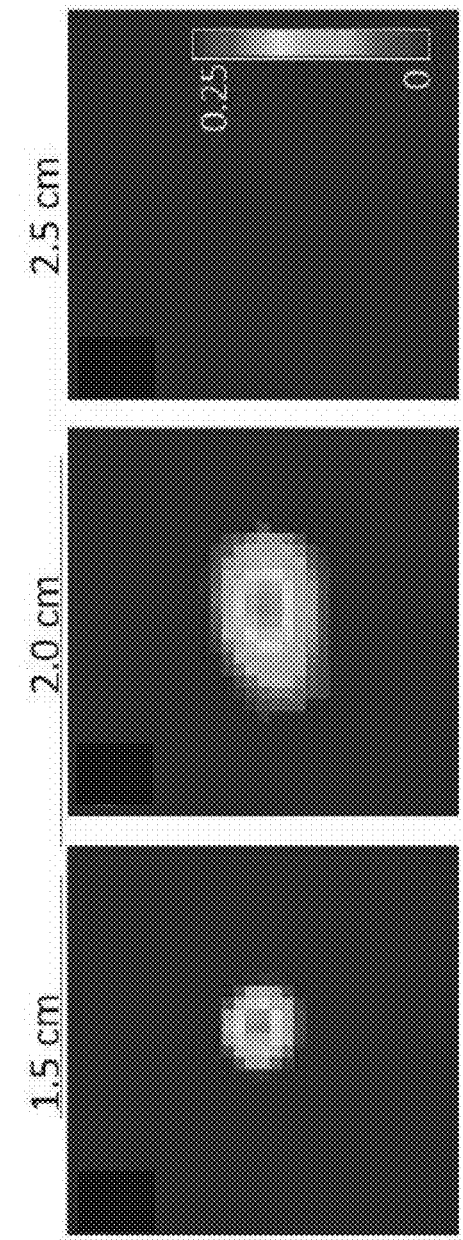
FIG. 4C is a reconstruction of one 2 cm diameter ball using a non-linear Born method.
Figure 5:
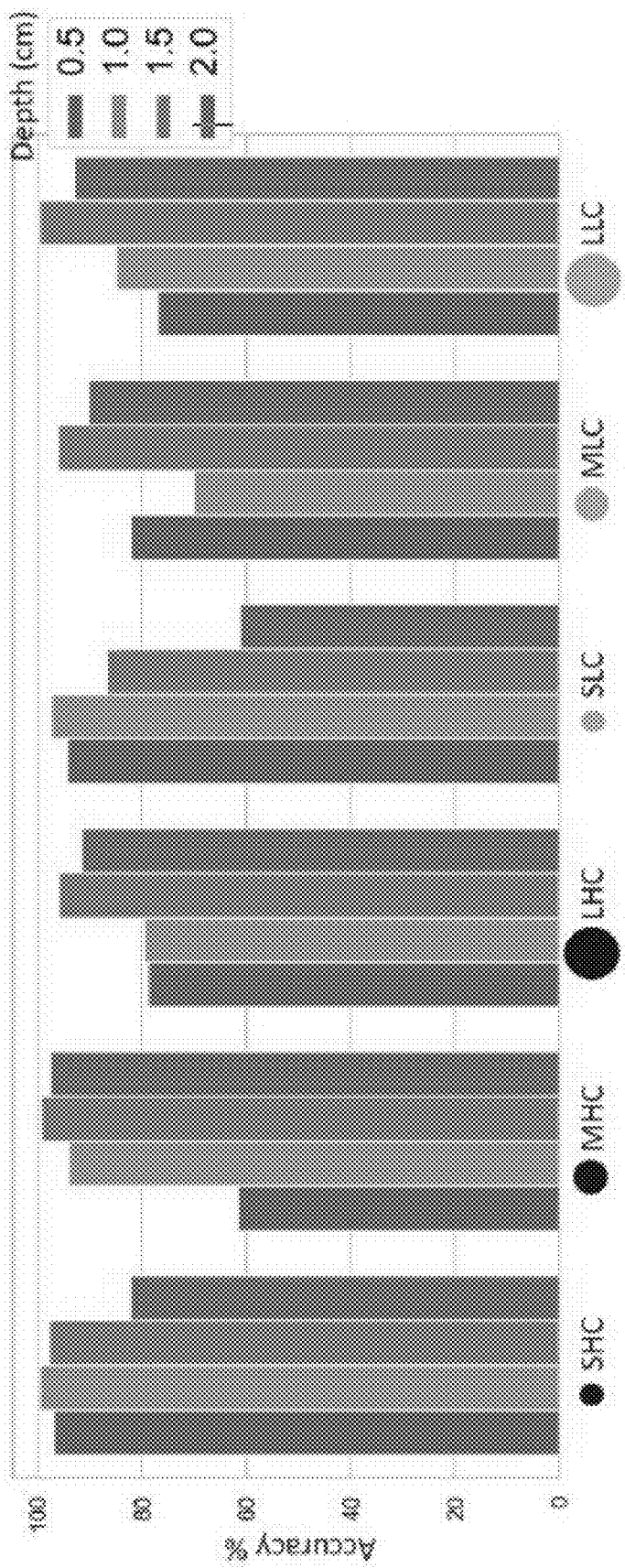
FIG. 5 is a bar graph showing comprehensive analysis of the accuracy of absorption coefficients of a phantom target.

Phantom experiments were performed with the methods described above. Reconstruction results were compared with the known first order linear Born method. FIG. 4A shows a 3D contour plot of the phantom target and FIG. 4B-4C show reconstructed images of a high optical contrast ball phantom located at 1.5 cm (top surface) depth inside the intralipid solution. The 3D absorption distribution is displayed as slices at different depths, labeled above each column: FIG. 4B is reconstruction of one 2 cm diameter ball using linear Born ($\mu_{a\ max}$=0.18 cm$^{-1}$) and FIG. 4C is reconstruction of one 2 cm diameter ball using a non-linear Born ($\mu_{a\ max}$=0.22 cm$^{-1}$). A more comprehensive analysis of the accuracy of absorption coefficients is shown in FIG. 5. HC and LC stand for high contrast ($\mu_a$=0.23 cm$^{-1}$) and low contrast ($\mu_a$=0.11 cm$^{-1}$), respectively. S, M, and L stand for small (1 cm diameter), medium (2 cm), and large (3 cm), respectively. The bars in the right upper legend indicate the depth of the top layer of the phantom target. The average absorption coefficients were estimated with 89.6% accuracy for high contrast phantoms and 86.1% for low contrast phantoms. The accuracy is calculated as $\mu_{a\ max}/\mu_{atruth}\times 100\%$.

Figure 6B:
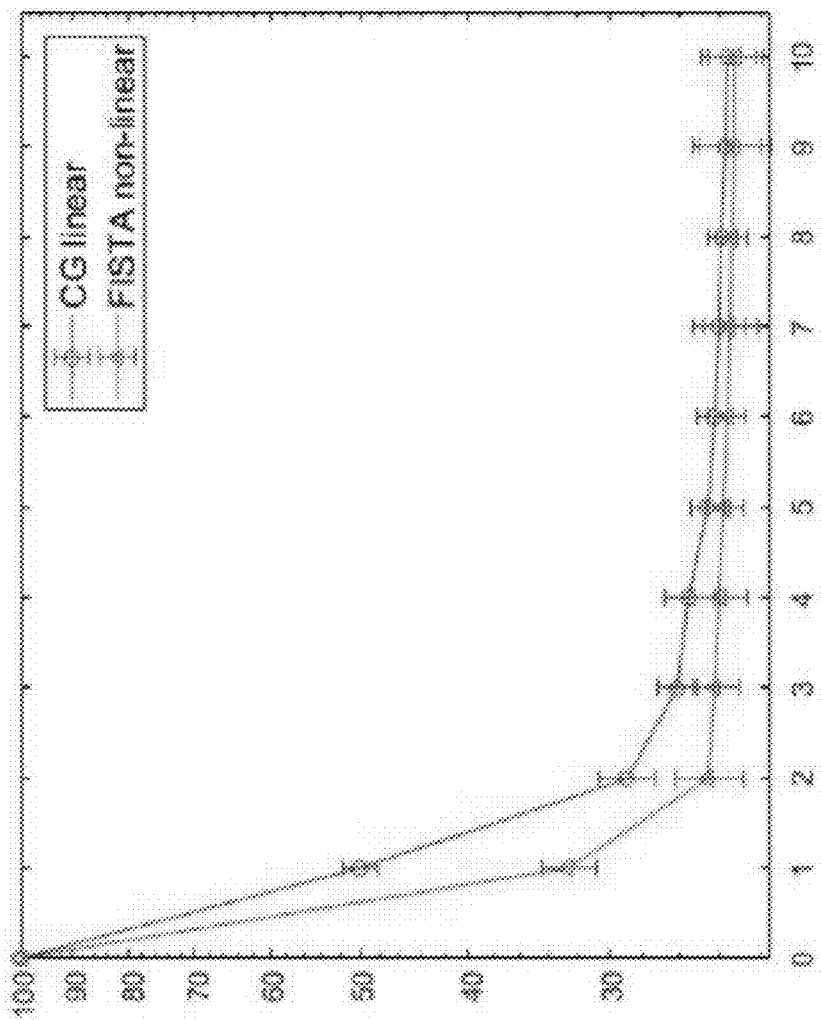
FIG. 6B is a graph showing the mean and standard deviation of least square errors (LSE) for both linear Born and non-linear Born methods plotted as a function of iterations.
Figure 6A:
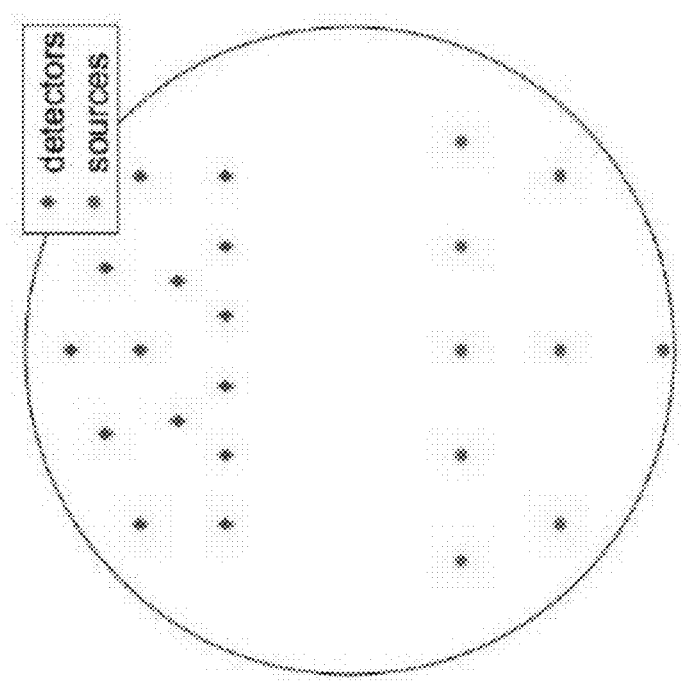
FIG. 6A is a schematic of the probe used for phantom experiments.

FIG. 6A shows the schematic of the probe used for phantom experiments. The iterative image reconstruction method using phantom data shown in FIG. 5 is analyzed for convergence. To compare the method with the conjugate gradient optimization method for linear Born, the least squares error (LSE) was normalized for each method to the power of the scattered field, $\|y\|^2$. The mean and standard deviation of least square errors (LSE) for each method are plotted as a function of iterations shown in FIG. 6B, where zero initialization is used for both methods. FISTA converges faster than the conjugate gradient method. On average, the objective function converges to a lower value for non-linear modeling, because more accurate estimation of the photon-density wave better fits the perturbed photon-density wave measurement $U_{sc}(r)$ in Eq. (3), reducing the LSE.

Figure 7:
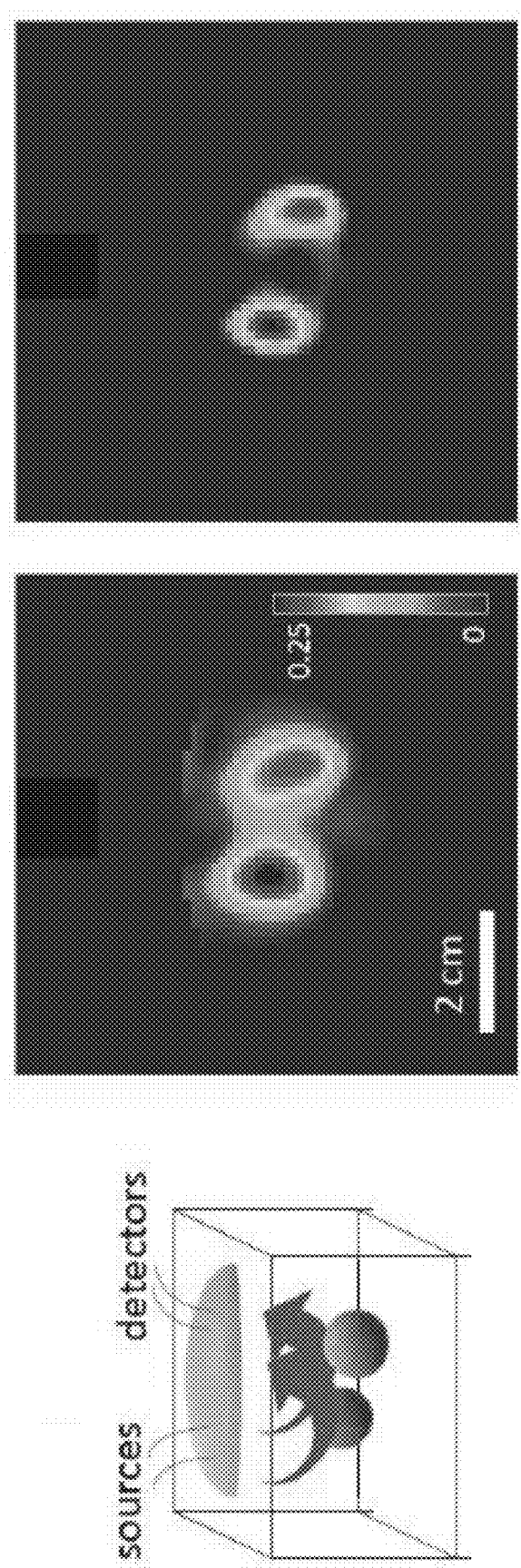
FIG. 7 illustrates the reconstruction experimental results using non-linear Born with regularization and linear Born without regularization.

Additionally, the resolution of reconstruction from non-linear Born with that from linear Born were compared by submerging two 1.0 cm diameter high contrast ($\mu_a$=0.23 cm$^{-1}$) ball shaped targets separated by 2 cm along the US B-scan direction inside the intralipid solution at 1.5 cm depth. FIG. 7 illustrates the experiment (left) and the reconstruction results using linear Born without regularization (middle) and non-linear Born with regularization (right). The non-linear Born algorithm with sparse regularization gives a smaller full width at half maximum (FWHM) value, which resolves the two targets much better than linear Born. This method does not require employing of two fine-grid regions, as discussed above.

Figure 8B:
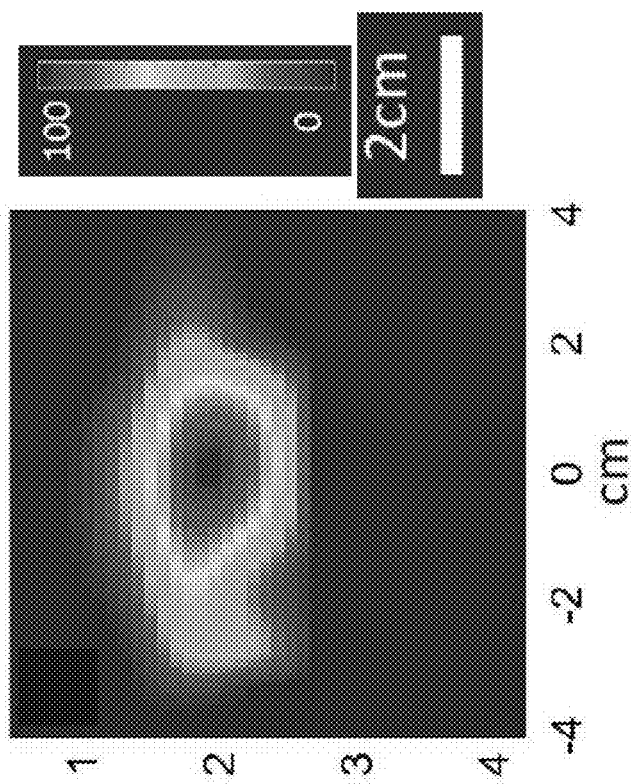
FIG. 8B is a center slice of a reconstructed tHb distribution at the orthogonal plane.
Figure 8A:
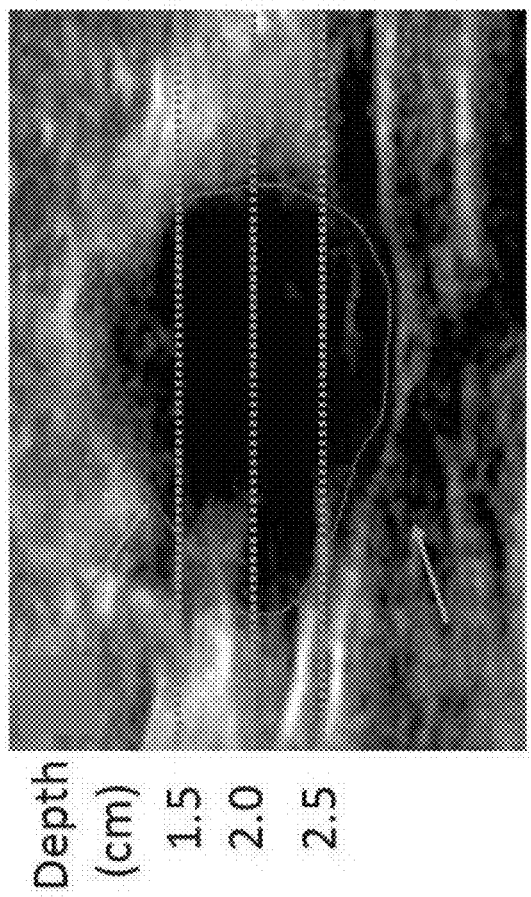
FIG. 8A is a co-registered US image.
Figure 8C:
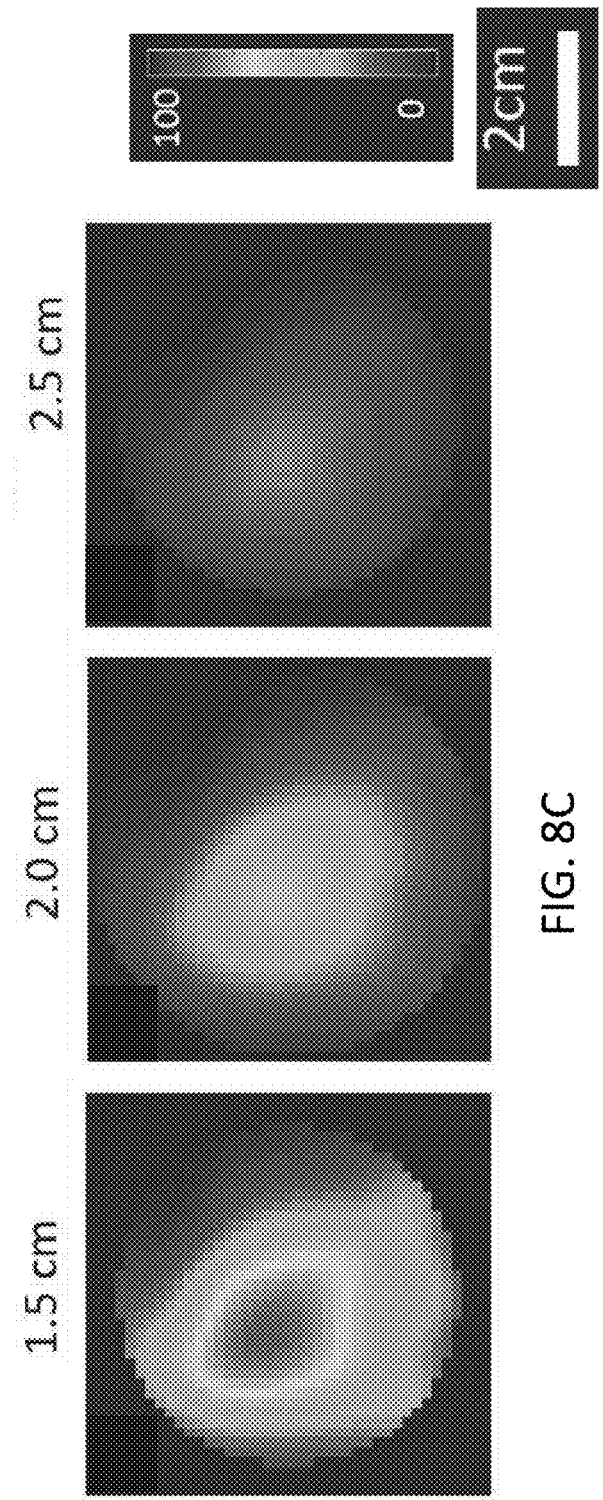
FIG. 8C shows reconstructed tHb concentration distributions using linear Born without regularization at maximum tHb=84.4 μM.
Figure 8D:
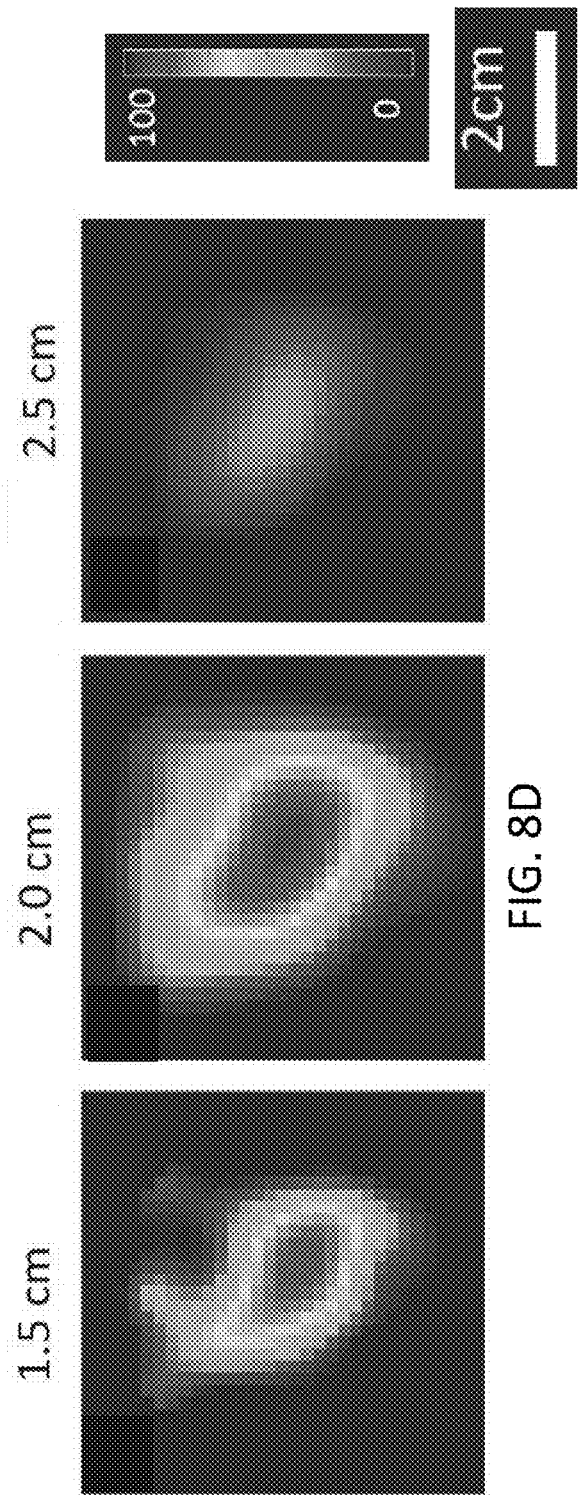
FIG. 8D shows reconstructed tHb concentration distributions using non-linear Born with regularization at maximum tHb=95.0 μM.
Figure 8E:
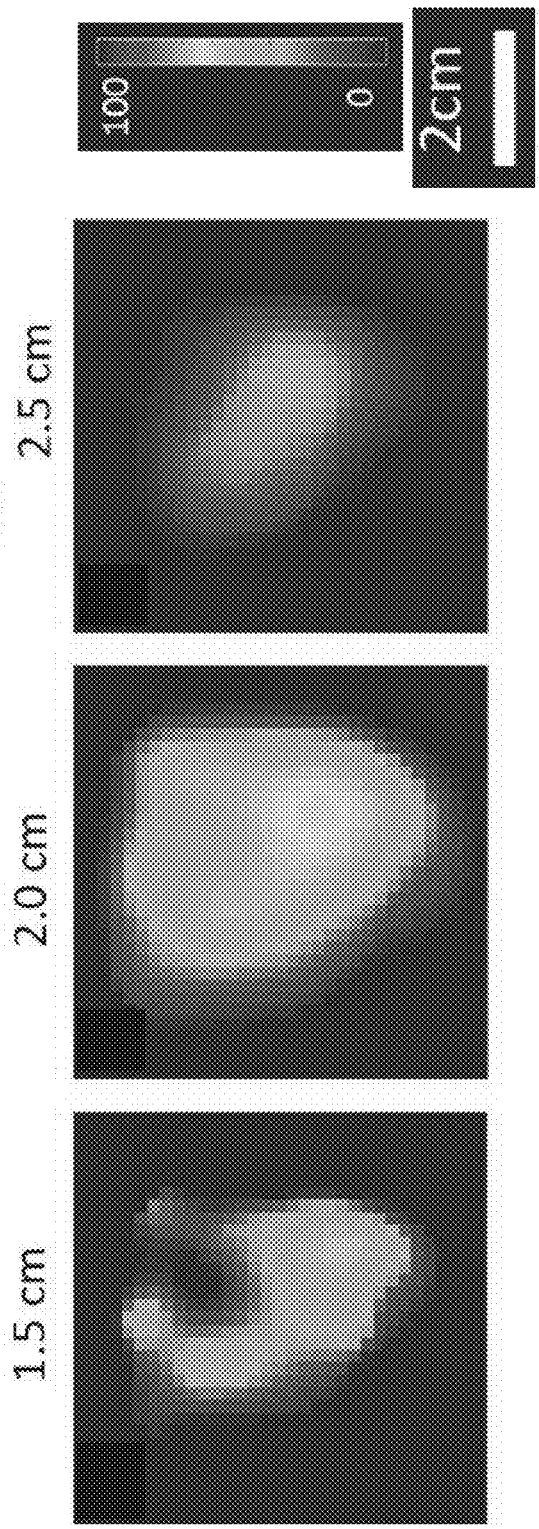
FIG. 8E shows reconstructed oxyHb concentration distributions using non-linear Born with regularization at maximum oxyHb=65.33 μM.
Figure 8F:
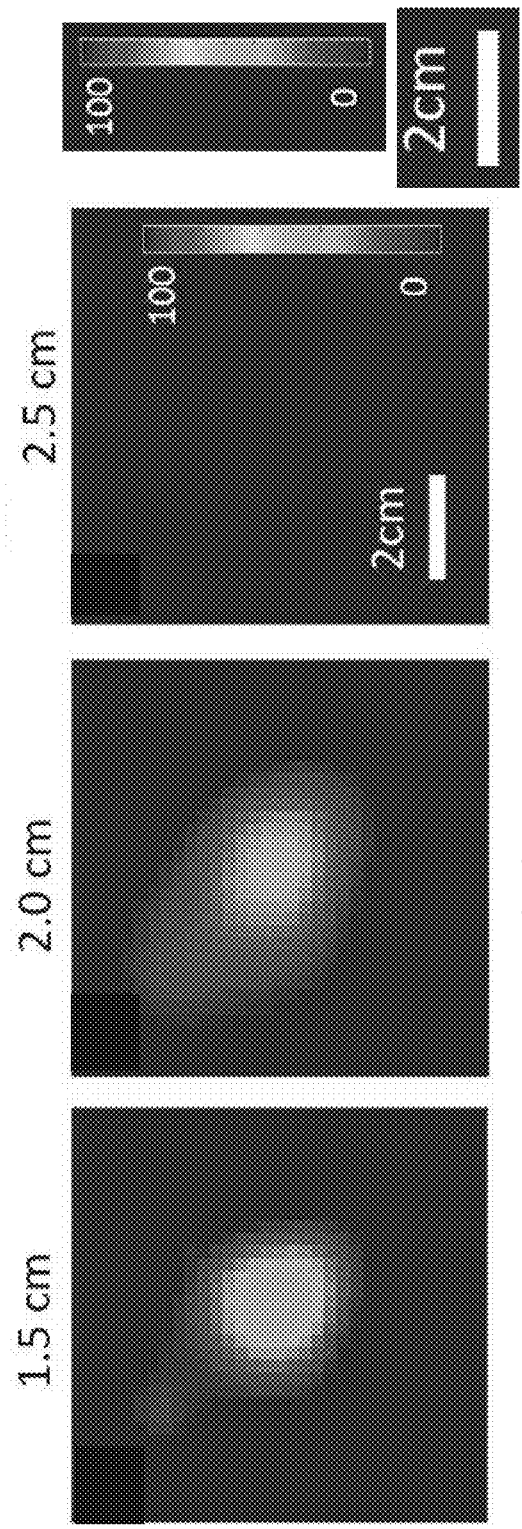
FIG. 8F shows reconstructed deoxyHb concentration distributions using non-linear Born with regularization at maximum deoxyHb=47.88 μM
Figure 9B:
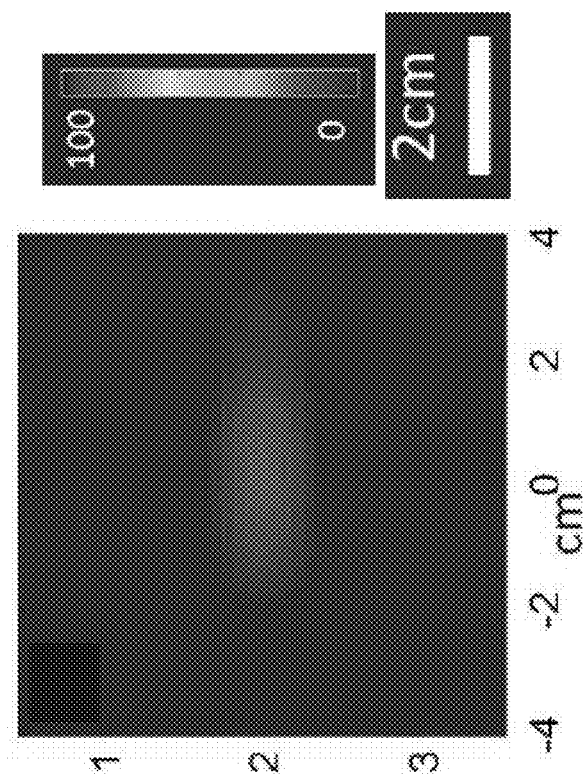
FIG. 9B is a center slice of a reconstructed tHb distribution at the orthogonal plane.
Figure 9A:
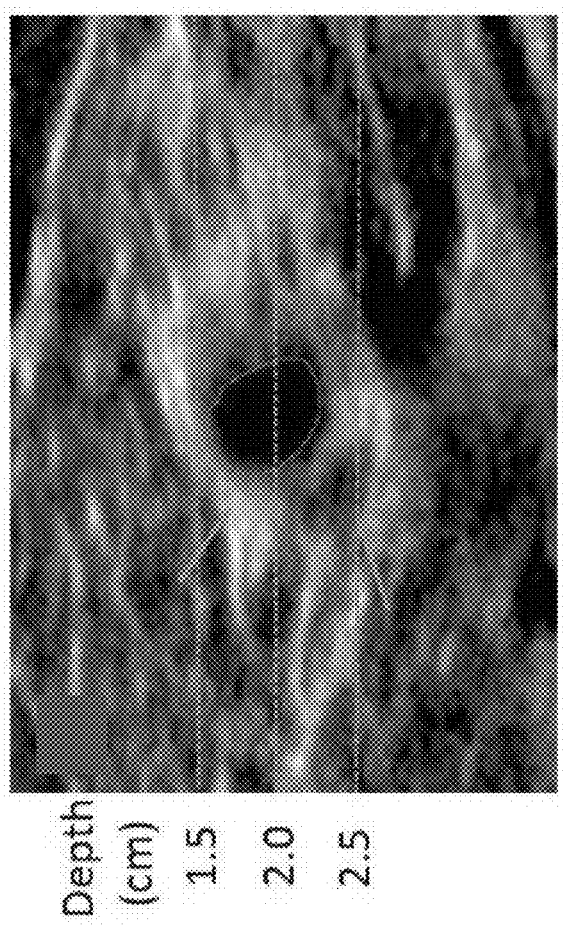
FIG. 9A is a co-registered US image.
Figure 9C:
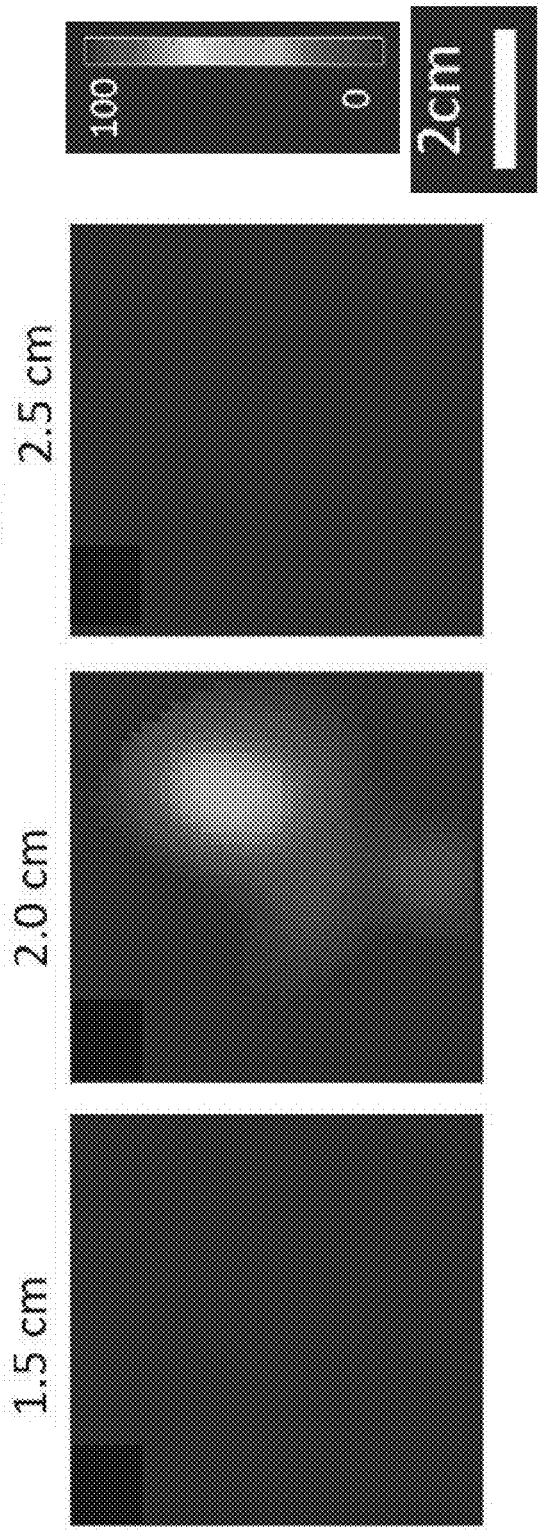
FIG. 9C shows reconstructed tHb concentration distributions using linear Born without regularization at maximum tHb=28.7 μM.
Figure 9D:
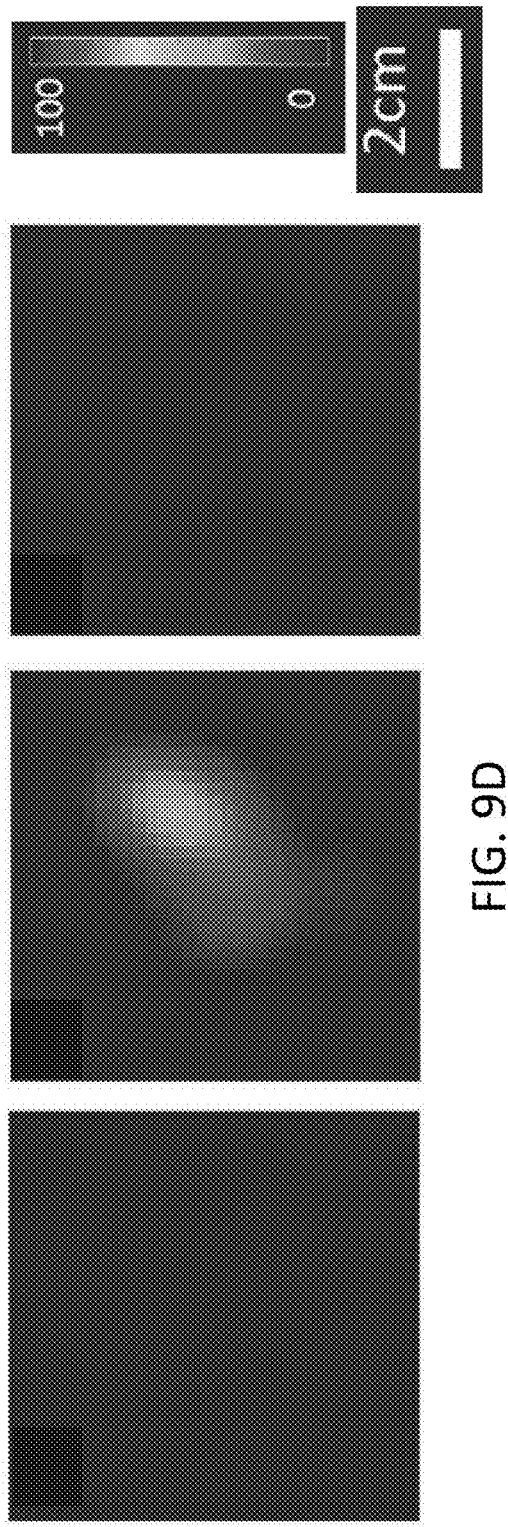
FIG. 9D shows reconstructed tHb concentration distributions using non-linear Born with regularization at maximum tHb=29.8 μM.
Figure 9E:
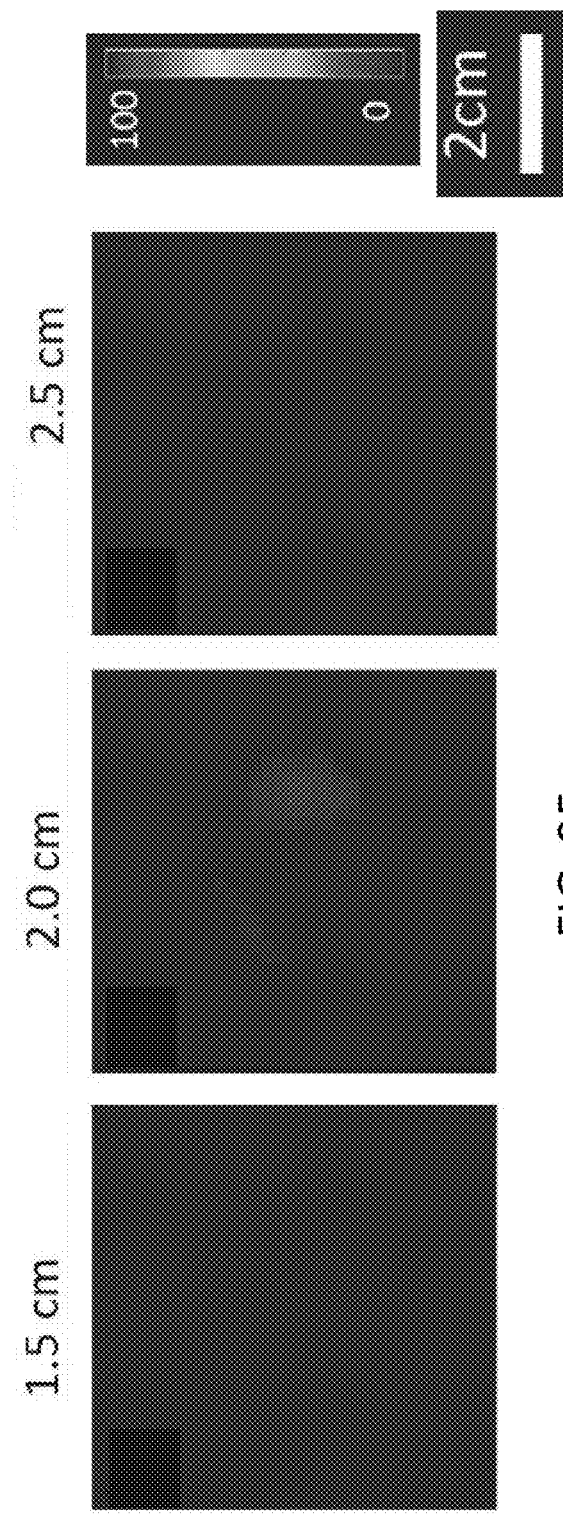
FIG. 9E shows reconstructed oxyHb concentration distributions using non-linear Born with regularization at maximum oxyHb=8.2 μM.
Figure 9F:
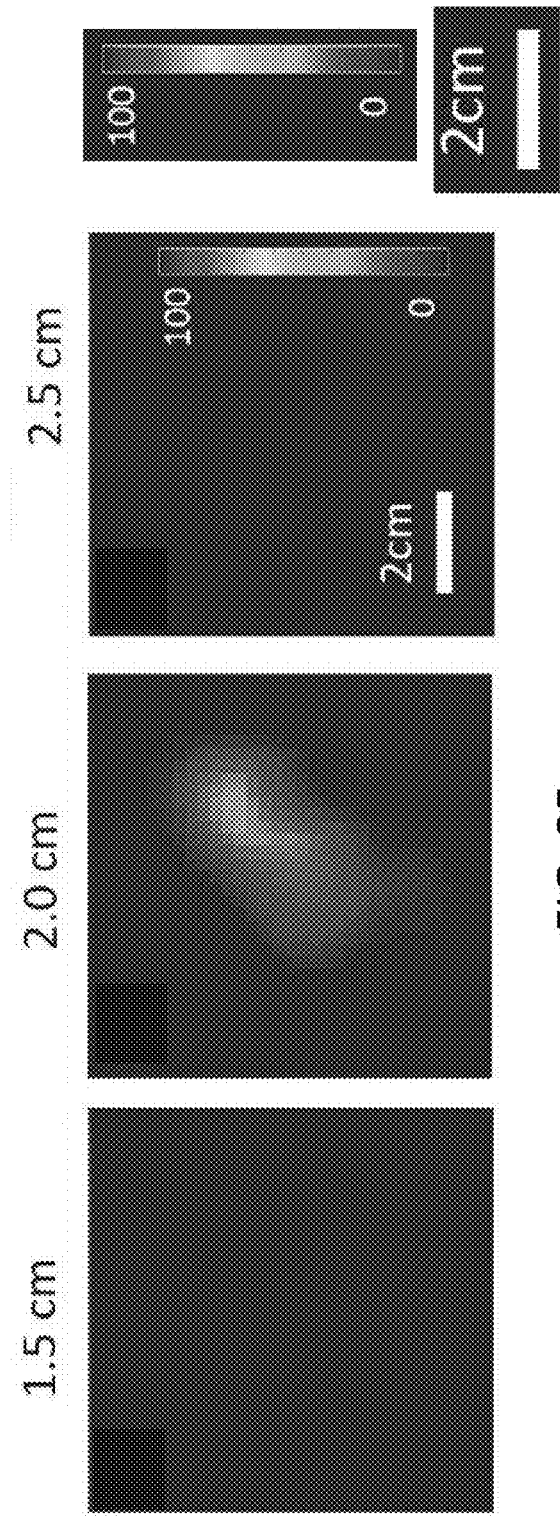
FIG. 9F shows reconstructed deoxyHb concentration distributions using non-linear Born with regularization at maximum deoxyHb=25.3 μM.
Figure 10:
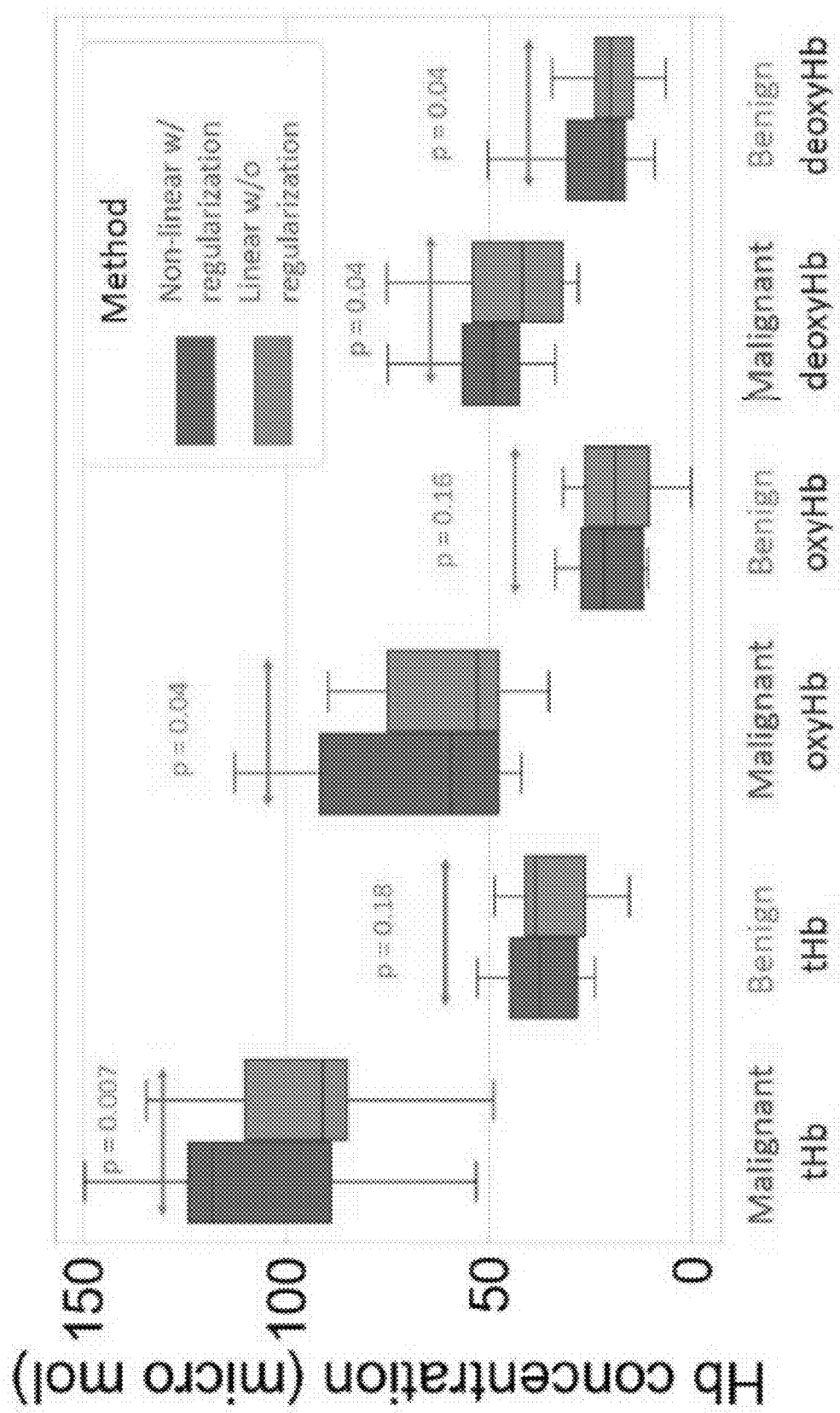
FIG. 10 is a box plot showing the statistics of the reconstructed functional maximum tHb, oxyHb, and deoxyHb values.

Non-linear Born was compared with linear Born across 20 patients, 10 with benign lesions and 10 with malignant ones. Patient data were acquired from the lesion side of the breast and the contralateral mirror position of the healthy breast. The perturbed photo-density wave was calculated as $$\frac{U_{lesion} - U_{reference}}{U_{reference}}, \qquad \text{Eq. (14)}$$

where $U_{lesion}$ and $U_{reference}$ are measurements from the lesion and reference breast, respectively. In the past, the use of a contralateral mirror position of a lesion breast were compared to a symmetric area of the same lesion breast as a healthy breast reference; however, the contralateral reference is more robust because the tissue curvature and the chest wall depth can be made symmetrical under the real-time assessment of co-registered ultrasound. FIG. 8A-8F show a reconstructed tHb, oxyHb, and deoxyHb map of a medium size malignant lesion. The tHb is calculated from absorption coefficients of four wavelengths, with the extinction coefficients for deoxygenated and oxygenated hemoglobin given in the literature. A co-registered US image is shown in FIG. 8A and indicates that the lesion is centered at 2 cm depth from the surface of the breast. A center slice of the reconstructed tHb distribution at the orthogonal plane is shown in FIG. 8B. The functional maximum tHb concentration reconstructed with non-linear Born and linear Born are 95.0 μM and 84.4 μM, respectively. FIG. 8C shows reconstructed tHb concentration distributions using linear Born without regularization at maximum tHb=84.4 μM. FIG. 8D shows reconstructed tHb concentration distributions using non-linear Born with regularization at maximum tHb=95.0 μM. FIG. 8E shows reconstructed oxyHb concentration distributions using non-linear Born with regularization at maximum oxyHb=65.33 μM. FIG. 8F shows reconstructed deoxyHb concentration distributions using non-linear Born with regularization at maximum deoxyHb=47.88 μM. The oxyHb distribution closely follows the tHb distribution, but is more heterogeneous, with slightly periphery enhancement. The deoxyHb distribution is more centered in the tumor core. This type of peripheral oxyHb distribution and core deoxyHb distribution is often seen in larger cancers due to the necrotic tissue in the center and rapid tumor growth at the periphery. FIG. 9A-9F show reconstruction results on a benign lesion, and the co-registered US image, as shown in FIG. 9A, suggests the lesion is located at 2 cm depth. The maximum tHb concentrations reconstructed with non-linear Born and linear Born are 29.8 μM and 28.7 μM, respectively. A center slice of the reconstructed tHb distribution at the orthogonal plane is shown in FIG. 9B. FIG. 9C shows reconstructed tHb concentration distributions using linear Born without regularization at maximum tHb=28.7 μM. FIG. 9D shows reconstructed tHb concentration distributions using non-linear Born with regularization at maximum tHb=29.8 μM. FIG. 9E shows reconstructed oxyHb concentration distributions using non-linear Born with regularization at maximum oxyHb=8.2 μM. FIG. 9F shows reconstructed deoxyHb concentration distributions using non-linear Born with regularization at maximum deoxyHb=25.3 μM. It is interesting to note that this benign lesion had higher deoxyHb than oxyHb, but both are low. This benign lesion is diagnosed as a proliferate lesion, which may account for the relatively higher deoxyHb component. Finally, the tHb, oxyHb, and deoxyHb values across all 20 cases were calculated. FIG. 10 illustrates the statistics of the reconstructed functional maximum tHb, oxyHb, and deoxyHb values in box plots. Again, non-linear Born is compared with linear Born. The non-linear Born algorithm improves the average malignant-to-benign lesion contrast ratio from 2.73 to 3.07, which is a 12.5% improvement. 12.4% improvement. For oxyHb and deoxyHb, the non-linear Born algorithm does not improve the average malignant-to-benign lesion ratio than that of linear Born. However, the mean oxyHb of non-linear Born of malignant group is higher than that of the linear Born (p=0.04), where p is the p-value from the t-test. The mean oxyHb of non-linear Born of benign group is statistically the same as the linear Born (p=0.16). This suggests that non-linear Born statistically improves the linear Born on oxyHb estimate for malignant group. For deoxyHb, non-linear Born improves deoxyHb than linear Born for both malignant and benign groups.

It has been experimentally demonstrated and validated that the proposed method can successfully reconstruct functional images of phantom targets and breast lesions. Phantom experiments confirm that the non-linear Born method yields better resolution and more accurate absorption coefficient distributions than the linear Born method.

In clinical cases, it is seen that non-linear Born reconstructs higher absorption coefficient value for large malignant cases than the linear Born method. Based on the results from 20 patients' data, the average malignant-to-benign lesion contrast is increased from 2.73, using the linear Born method, to 3.07, which is a 12.5% improvement. For lesions approximately more than 2.0 cm in diameter, the average malignant-to-benign contrast is increased from 2.68 to 3.31, which is a 23.5% improvement. This method can achieve more faithful results than the linear Born method because the photon-density wave attenuation is calculated more accurately with the iterative update, and the US a priori structure information is incorporated adequately through sparsity-promoting regularization. Moreover, the method also presents more realistic tumor absorption distributions.

To conclude, the proposed non-linear Born method with US-guided shape regularization significantly improves the reconstructed target shape, accuracy, and resolution. The method uses a non-linear forward model for better photon-density distribution estimation and a fast converging algorithm for solving the inverse problem, incorporating lesion structure information provided by the US image. Moreover, with selective modifications, the method is also applicable to MRI- or X-ray-guided DOT.

Embodiments of the disclosure, such as non-linear Born method with US-guided depth regularization may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein. Aspects of the disclosure may also be practiced in distributed computing environments where tasks are performed by remote processing devices that are linked through a communications network. In a distributed computing environment, program modules may be located in both local and remote computer storage media including memory storage devices.

The computer systems, computing devices, and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on vehicle or mobile devices, or associated with smart infrastructure or remote servers), and/or via computer executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may include but are not limited to: images or frames of a video, object characteristics, and object categorizations. Data inputs may further include: sensor data, image data, video data, telematics data, authentication data, authorization data, security data, mobile device data, geolocation information, transaction data, personal identification data, financial data, usage data, weather pattern data, "big data" sets, and/or user preference data. ML outputs may include but are not limited to: a tracked shape output, categorization of an object, categorization of a type of motion, a diagnosis based on motion of an object, motion analysis of an object, and trained model parameters ML outputs may further include: speech recognition, image or video recognition, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some aspects, data inputs may include certain ML outputs.

In some aspects, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, and reinforcement learning.

In one aspect, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function which maps outputs to inputs and utilize the predictive function to generate ML outputs based on data inputs. The example inputs and example outputs of the training data may include any of the data inputs or ML outputs described above. For example, a ML module may receive training data comprising customer identification and geographic information and an associated customer category, generate a model which maps customer categories to customer identification and geographic information, and generate a ML output comprising a customer category for subsequently received data inputs including customer identification and geographic information.

In another aspect, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship. In one aspect, a ML module receives unlabeled data comprising customer purchase information, customer mobile device information, and customer geolocation information, and the ML module employs an unsupervised learning method such as "clustering" to identify patterns and organize the unlabeled data into meaningful groups. The newly organized data may be used, for example, to extract further information about a customer's spending habits.

In yet another aspect, ML methods and algorithms are directed toward reinforcement learning, which involves optimizing outputs based on feedback from a reward signal. Specifically ML methods and algorithms directed toward reinforcement learning may receive a user-defined reward signal definition, receive a data input, utilize a decision-making model to generate a ML output based on the data input, receive a reward signal based on the reward signal definition and the ML output, and alter the decision-making model so as to receive a stronger reward signal for subsequently generated ML outputs. The reward signal definition may be based on any of the data inputs or ML outputs described above. In one aspect, a ML module implements reinforcement learning in a user recommendation application. The ML module may utilize a decision-making model to generate a ranked list of options based on user information received from the user and may further receive selection data based on a user selection of one of the ranked options. A reward signal may be generated based on comparing the selection data to the ranking of the selected option. The ML module may update the decision-making model such that subsequently generated rankings more accurately predict a user selection.

As will be appreciated based upon the foregoing specification, the above-described aspects of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

What is claimed is:

1. A diffuse optical tomography (DOT) system for generating a functional image of a lesion region of a subject, comprising:
    a source subsystem configured to generate optical waves;
    a probe coupled to the source subsystem and configured to emit the optical waves generated by the source subsystem toward the lesion region and to detect optical waves reflected by the lesion region;
    a detection subsystem configured to convert the optical waves detected by the probe to digital signals; and
    a computing device including a processor and a memory, the memory including instructions that program the processor to:
        receive the digital signals sent from the detection subsystem;
        receive lesion depth and shape information from a plurality of co-registered ultrasound images of the lesion region;
        calculate an initial estimate of the functional image based on the digital signals and the lesion depth and shape information by solving an inverse optimization problem with a target-shape-regularized Fast Iterative Shrinkage-Thresholding algorithm (FISTA), wherein the calculation of the initial estimate is based upon depth dependent $\ell 1$ regularization;
        generate the functional image of the lesion region of the subject by performing a depth dependent $\ell 1$ regularized non-linear Born iterative reconstruction method that comprises a non-linear Born iterative reconstruction method regularized by the depth dependent $\ell 1$ regularization associated with the initial estimate, the functional image being generated by the processor being further programmed by the instructions to:
            (1) generate, as part of the functional image, a lesion absorption map based on the initial estimate by solving the inverse optimization problem with the target-shape-regularized FISTA;
            (2) update, using a Finite Difference Method (FDM), a photon-density wave distribution associated with the initial estimate to obtain an updated estimation of a weight matrix for use with the depth dependent $\ell 1$ regularized non-linear Born iterative reconstruction method;
            (3) generate an updated weight matrix based at least on the updated estimation of the weight matrix; and
            (4) perform at least two iterations of the depth dependent $\ell 1$ regularized non-linear Born iterative reconstruction method, at least one of the at least two iterations using the updated weight matrix; and
        display the generated functional image.

2. The DOT system of claim 1, wherein the instructions program the processor to calculate an initial estimate of the functional image using a dual-grid schedule to discretize the legion region with a fine grid and to discretize the background volume of the subject with a coarse grid to generate a weighted matrix for the lesion region and a weighted matrix for the background volume based on absorption of the optical waves on the subject.

3. The DOT system of claim 2, wherein the instructions program the processor to perform reconstruction via the depth dependent $\ell 1$ regularized non-linear Born iterative reconstruction method for generating the functional image iteratively by updating the photon-density wave distribution with a conjugate gradient method inside the fine grid.

4. The DOT system of claim 1, further comprising an ultrasound imaging device coupled to the computing device and configured to generate the plurality of co-registered ultrasound images of the lesion region.

5. The DOT system of claim 1, wherein the source subsystem is configured to generate optical waves at four optical wavelengths in a range from 730 nm to 830 nm.

6. The DOT system of claim 1, wherein the depth dependent $\ell 1$ regularized non-linear Born iterative reconstruction method is configured to reconstruct at least one of values or distributions of absorption coefficients associated with absorption of the optical waves on the subject.

7. A method for generating a functional image of a lesion region of a subject using diffuse optical tomography (DOT), the method comprising:
    emitting optical waves toward the lesion region;
    detecting optical waves reflected by the lesion region and converting the optical waves to digital signals;
    receiving lesion depth and shape information from a plurality of co-registered ultrasound images of the lesion region;
    calculating an initial estimate of the functional image based on the digital signals and the lesion depth and shape information by solving an inverse optimization problem with a shape-regularized Fast Iterative Shrinkage-Thresholding algorithm (FISTA), wherein the calculation of the initial estimate is based upon depth dependent $\ell 1$ regularization;
    generating the functional image of the lesion region the subject by performing a depth dependent $\ell 1$ regularized non-linear Born iterative reconstruction method that comprises a non-linear Born iterative reconstruction method regularized by the depth dependent $\ell 1$ regularization associated with the initial estimate, by:

(1) generating, as part of the functional image, a lesion absorption map based on the initial estimate by solving the inverse optimization problem with the target-shape-regularized FISTA;

(2) updating, using a Finite Difference Method (FDM), a photon-density wave distribution associated with the initial estimate to obtain an updated estimation of a weight matrix for use with the depth dependent $\ell 1$ regularized non-linear Born iterative reconstruction method;

(3) generating an updated weight matrix based at least on the updated estimation of the weight matrix; and (4) performing at least two iterations of the depth dependent $\ell 1$ regularized non-linear Born iterative reconstruction method, at least one of the at least two iterations using the updated weight matrix; and displaying the generated functional image.

8. The method of claim 7, further comprising calculating an initial estimate of the functional image using a dual-grid schedule to discretize the legion region with a fine grid and to discretize the background volume of the subject with a coarse grid to generate a weighted matrix for the lesion region and a weighted matrix for the background volume based on absorption of the optical waves on the subject.

9. The method of claim 8, further comprising performing reconstructing via the depth dependent $\ell 1$ regularized non-linear Born iterative reconstruction method for generating the functional image iteratively by updating the photon-density wave distribution with a conjugate gradient method inside the fine grid.

10. The method of claim 7, further comprising generating optical waves at four optical wavelengths in a range from 730 nm to 830 nm.

11. The method of claim 7, wherein the depth dependent $\ell 1$ regularized non-linear Born iterative reconstruction method is configured to reconstruct at least one of values or distributions of absorption coefficients associated with absorption of the optical waves on the subject.

12. At least one non-transitory computer-readable storage media having computer-executable instructions embodied thereon for generating a functional image of a lesion region of a subject using diffuse optical tomography (DOT), wherein when executed by at least one processor, the computer-executable instructions cause the processor to:

emit optical waves toward a lesion region of the subject;

detect optical waves reflected by the lesion region and converting the optical waves to digital signals;

receive lesion depth and shape information from a plurality of co-registered ultrasound images of the lesion region;

calculate an initial estimate of the functional image based on the digital signals and the lesion depth and shape information by solving an inverse optimization problem with a shape-regularized Fast Iterative Shrinkage-Thresholding algorithm (FISTA), wherein the calculation of the initial estimate is based upon depth dependent $\ell 1$ regularization;

generate the functional image of the lesion region of the subject by performing a depth dependent $\ell 1$ regularized non-linear Born iterative reconstruction method that comprises non-linear Born iterative reconstruction method regularized by the depth dependent $\ell 1$ regularization associated with the initial estimate, the functional image being generated by the processor being further caused by the computer-executable instructions to:

(1) generate, as part of the functional image, a lesion absorption map based on the initial estimate by solving the inverse optimization problem with the target-shape-regularized FISTA;

(2) update, using a Finite Difference Method (FDM), a photon-density wave distribution associated with the initial estimate to obtain an updated estimation of a weight matrix for use with the depth dependent $\ell 1$ regularized non-linear Born iterative reconstruction method;

(3) generate an updated weight matrix based at least on the updated estimation of the weight matrix; and (4) perform at least two iterations of the depth dependent $\ell 1$ regularized non-linear Born iterative reconstruction method, at least one of the at least two iterations using the updated weight matrix; and display the generated functional image.

13. The computer-readable storage medium of claim 12, wherein the computer-executable instructions further cause the processor to calculate an initial estimate of the functional image using a dual-grid schedule to discretize the legion region with a fine grid and to discretize the background volume of the subject with a coarse grid to generate a weighted matrix for the lesion region and a weighted matrix for the background volume based on absorption of the optical waves on the subject.

14. The computer-readable storage medium of claim 13, wherein the computer-executable instructions further cause the processor to perform reconstruction via the depth dependent $\ell 1$ regularized non-linear Born iterative reconstruction method for generating the functional image iteratively by updating the photon-density wave distribution with a conjugate gradient method inside the fine grid.

15. The computer-readable storage medium of claim 12, wherein the computer-executable instructions further cause the processor to receive the plurality of co-registered ultrasound images of the lesion region from an ultrasound imaging device.

16. The computer-readable storage medium of claim 12, wherein the computer-executable instructions further cause the processor to generate near-infrared (NIR) optical waves at four optical wavelengths in a range from 730 nm to 830 nm.

17. The computer-readable storage medium of claim 12, wherein the depth dependent $\ell 1$ regularized non-linear Born iterative reconstruction method is configured to reconstruct at least one of values or distributions of absorption coefficients associated with absorption of the optical waves on the subject.

* * * * *